United States Patent
Bredif et al.

(10) Patent No.: US 10,196,607 B2
(45) Date of Patent: Feb. 5, 2019

(54) RECONSTITUTED NIPPLE SKIN MODEL

(71) Applicant: Laboratoires Expanscience, Courbevoie (FR)

(72) Inventors: Stephanie Bredif, Croisilles (FR); Caroline Baudouin, Rambouillet (FR); Philippe Msika, Versailles (FR); Marisa Meloni, Milan (IT)

(73) Assignee: LABORATOIRES EXPANSCIENCE, Paris la Defense (FR)

( * ) Notice: Subject to any disclaimer, the term of this patent is extended or adjusted under 35 U.S.C. 154(b) by 37 days.

(21) Appl. No.: 15/110,826

(22) PCT Filed: Jan. 12, 2015

(86) PCT No.: PCT/EP2015/050422
§ 371 (c)(1),
(2) Date: Jul. 11, 2016

(87) PCT Pub. No.: WO2015/104413
PCT Pub. Date: Jul. 16, 2015

(65) Prior Publication Data
US 2016/0326492 A1   Nov. 10, 2016

(30) Foreign Application Priority Data

Jan. 10, 2014 (FR) .................. 14 50193

(51) Int. Cl.
| | | |
|---|---|---|
| *C12N 9/04* | (2006.01) | |
| *C07K 14/52* | (2006.01) | |
| *C07K 14/78* | (2006.01) | |
| *C12N 5/071* | (2010.01) | |
| *G01N 33/50* | (2006.01) | |
| *C07K 14/495* | (2006.01) | |

(52) U.S. Cl.
CPC .......... *C12N 5/0629* (2013.01); *C07K 14/495* (2013.01); *C07K 14/52* (2013.01); *C07K 14/78* (2013.01); *C12N 5/0698* (2013.01); *C12N 9/0006* (2013.01); *G01N 33/5082* (2013.01); *G01N 33/5088* (2013.01); *C12N 2533/54* (2013.01); *G01N 2333/47* (2013.01); *G01N 2333/495* (2013.01); *G01N 2333/525* (2013.01); *G01N 2333/7055* (2013.01); *G01N 2333/904* (2013.01)

(58) Field of Classification Search
None
See application file for complete search history.

(56) References Cited

U.S. PATENT DOCUMENTS

| | | |
|---|---|---|
| 4,849,077 A | 7/1989 | Rosenthal et al. |
| 4,882,127 A | 11/1989 | Rosenthal et al. |
| 6,723,513 B2 | 4/2004 | Lexow |
| 7,556,922 B2 | 7/2009 | Block et al. |
| 2006/0275782 A1 | 12/2006 | Gunderson et al. |
| 2007/0148771 A1 | 6/2007 | Chopart et al. |
| 2008/0020392 A1 | 1/2008 | Block et al. |
| 2009/0181385 A1 | 7/2009 | McKernan et al. |
| 2009/0181860 A1 | 7/2009 | McKernan et al. |
| 2009/0186349 A1 | 7/2009 | Gunderson et al. |
| 2010/0099576 A1 | 4/2010 | Comer et al. |

FOREIGN PATENT DOCUMENTS

| | | |
|---|---|---|
| EP | 0 029 678 A1 | 6/1981 |
| EP | 0 285 471 A1 | 10/1988 |
| EP | 0 789 074 A1 | 8/1997 |
| EP | 1 141 399 B1 | 10/2001 |
| EP | 1 451 302 B1 | 9/2004 |
| EP | 1 878 790 A1 | 1/2008 |
| EP | 1 974 718 A1 | 10/2008 |
| FR | 2 822 821 A1 | 10/2002 |
| FR | 2 857 596 A1 | 1/2005 |
| WO | WO-98/47479 A1 | 10/1998 |
| WO | WO-01/21605 A2 | 3/2001 |
| WO | WO-01/51596 A2 | 7/2001 |
| WO | WO-02/070729 A2 | 9/2002 |
| WO | WO-03/066896 A2 | 8/2003 |
| WO | WO-2004/012496 A2 | 2/2004 |
| WO | WO-2004/012752 A2 | 2/2004 |
| WO | WO-2004/016106 A1 | 2/2004 |
| WO | WO-2004/050052 A1 | 6/2004 |
| WO | WO-2004/050079 A1 | 6/2004 |
| WO | WO-2004/112741 A1 | 12/2004 |

(Continued)

OTHER PUBLICATIONS

Howell et al., J Allergy Clin. Immunol., 2007, vol. 20, p. 150-155.*

(Continued)

*Primary Examiner* — Kade Ariani
(74) *Attorney, Agent, or Firm* — Potomac Law Group, PLLC

(57) ABSTRACT

A skin model comprises keratinocytes capable of overexpressing filaggrin. A method for evaluating the in vitro activity of a formulation or of at least one active agent on the healing of nipple skin and/or on the reduction of nipple skin inflammation, by bringing said active agent or said formulation into contact with a skin model comprising keratinocytes overexpressing filaggrin and also comprising a lesion, and measuring the level of production of at least one biological marker chosen from lactate dehydrogenase (LDH), TNFα, filaggrin, TGFβ1 and β1 integrin.

21 Claims, 6 Drawing Sheets

(56) References Cited

FOREIGN PATENT DOCUMENTS

Figure 1:
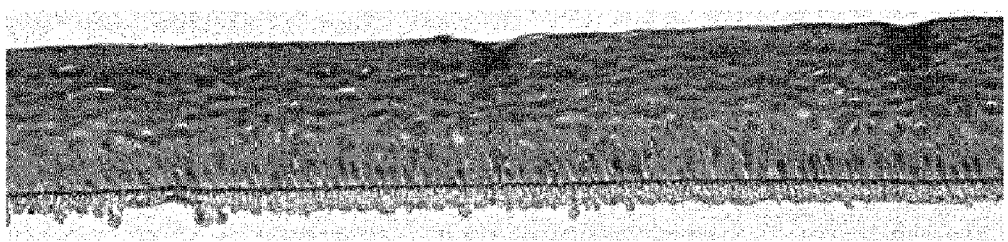

| WO | WO-2004/112742 A2 | 12/2004 |
|---|---|---|
| WO | WO-2005/102259 A1 | 11/2005 |
| WO | WO-2005/105123 A1 | 11/2005 |
| WO | WO-2005/115421 A1 | 12/2005 |
| WO | WO-2006/063864 A2 | 6/2006 |
| WO | WO-2006/063865 A2 | 6/2006 |
| WO | WO-2006/084132 A2 | 8/2006 |
| WO | WO-2007/057439 A1 | 5/2007 |
| WO | WO-2007/064305 A1 | 6/2007 |
| WO | WO-2007/111924 A1 | 10/2007 |
| WO | WO-2008/009709 A1 | 1/2008 |
| WO | WO-2008/080974 A1 | 7/2008 |
| WO | WO-2013/014435 A1 | 1/2013 |

OTHER PUBLICATIONS

"Atopic Dermatitis" by Susan Haller Psaila MD, in Pediatric Clinical Advisor, Instant Diagnosis and Treatment, 2nd Edition, 2007, Edited by: Lynn C. Garfunkel, MD, Jeffrey M. Kaczorowski, MD, and Cynthia Christy, MD, p. 60.*

Definition of "Model" according to Google online dictionary, retrieved on Jun. 28, 2018.*

Keratinocytes from Wikipedia, retrieved on Jun. 28, 2018, 6 pages.*

Mehul et al., Gene expression profiles of three different models of reconstructed human epidermis and classical cultures of keratinocytes using cDNA arrays, Arch. Dermatol. Res., vol. 296, pp. 145-156, 2004.

Boelsma et al., "Characterization and Comparison of Reconstructed Skin Models: Morphological and Immunohistochemical Evaluation," Acta Derm Venereol, vol. 80, pp. 82-88, 2000.

Ponec et al., "Characterization of Reconstructed Skin Models," Skin Pharmacol. Appl. Skin Physiol., vol. 15 (suppl. 1), pp. 4-17, 2002.

Auxenfans et al., "Adipose-derived stem cells (ASCs) as a source of endothelial cells in the reconstruction of endothelialized skin equivalents," Journal of Tissue Engineering and Regenerative Medicine, vol. 6, 2012, pp. 512-518.

Auxenfans et al., "Evolution of three dimensional skin equivalent models reconstructed in vitro by tissue engineering," Eur J Dermatol, vol. 19, No. 2, 2009, pp. 107-113.

Bechetoille et al., "Effects of Solar Ultraviolet Radiation on Engineered Human Skin Equivalent Containing Both Langerhans Cells and Dermal Dendritic Cells," vol. 13, No. 11, 2007, pp. 2667-2679.

Black et al., "Optimization and Characterization of an Engineered Human Skin Equivalent," Tissue Engineering, vol. 11, No. 5/6, 2005, pp. 723-733.

Bouwstra et al., "Water Distribution and Natural Moisturizer Factor Content in Human Skin Equivalents are regulated by Environmental Relative Humidity," Journal of Investigative Dermatology, 2007, pp. 378-388.

Costin et al., "Vaginal Irritation Models: The Current Status of Available Alternative and In Vitro Tests" ATLA, vol. 39, 2011, pp. 317-337.

Dongari-Bagtzoglou et al., "Development of a highly reproducible three-dimensional organotypic model of the oral mucosa," Nat Protoc., vol. 1, No. 4, 2006, 15 pages.

Eisenberg et al., "Human housekeeping genes are compact," Trends in Genetics, vol. 19, No. 7, Jul. 2003, pp. 362-365.

Fuller et al., "The challenges of sequencing by synthesis," Nature Biotechnology, vol. 27, No. 11, 2009, pp. 1015-1023.

Harding et al., "Filaggrin revisited" International Journal of Cosmetic Science, vol. 35, No. 5., 2003, pp. 412-423.

Horiguchi et al., "Ultrastructural and immunohistochemical characterization of basal cells in three-dimensional culture models of the skin," Archives of Dermatological Research, vol. 286, 1994, pp. 53-61.

Kinikoglu et al., "Reconstruction of a full-thickness collagen-based human oral mucosal equivalent," Biomaterials, vol. 30, 2009, pp. 6418-6425.

Kinikoglu et al., "The influence of elastin-like recombinant polymer on the self-renewing potential of a 3D tissue equivalent derived from human lamina propria fibroblasts and oral epithelial cells," Biomaterials, vol. 32, 2011, pp. 5756-5764.

Lequeux et al., "A Simple Way to Reconstruct a Human 3-D Hypodermis: A Useful Tool for Pharmacological Functionality," Skin Pharmacology and Physiology, vol. 25, No. 1, 2012, pp. 47-55.

Mahler et al., "Keratin 2e: A Marker for Murine Nipple Epidermis," Cells Tissues Organs, vol. 176, No. 4, 2004, pp. 169-177.

Mardis, Elaine, "New strategies and emerging technologies for massively parallel sequencing applications in medical research," vol. 1, No. 4, 2009, 4 pages.

Fortunel et al., "Cellular Adhesion on collagen: A simple method to select human basal keratinocytes which preserves their high growth capacity," European journal of dermatology, May 2011, 26 pages.

Metzker, Michael, "Sequencing technologies-the next generation," Nature Reviews: Genetics, vol. 11, 2010, pp. 31-46.

Panchal et al., "Neuregulin3 alters cell fate in the epidermis and mammary gland," BMC Developmental Biology, vol. 7, No. 105, 2007, 21 pages.

Pihlak et al., "Rapid genome sequencing with short universal tiling probes," Nature Biotechnology, vol. 26, No. 6, 2008, pp. 676-684.

Ponec et al., "Lipid and ultrastructural characterization of reconstructed skin models," International Journal of Pharmaceutics, vol. 203, No. 1-2, 2000, pp. 211-225.

Ponec et al., "The Formation of Competent Barrier Lipids in Reconstructed Human Epidermis Requires the Presence of Vitamin C," vol. 193, No. 3, 1997, pp. 348-355.

Rosdy et al., "Retinoic Acid Inhibits Epidermal Differentiation When Applied Topically on the Stratum Corneum of Epidermis Formed in Vitro by Human Keratinocytes Grown on Defined Medium," In Vitro Toxicology, vol. 10, No. 1, 1997, pp. 39-47.

Schmalz et al., "Release of prostaglandin E2, IL-6 and IL-8 from human oral epithelial culture models after exposure to compounds of dental materials," European Journal of Oral Sciences, vol. 108, No. 5, 2008, pp. 442-448.

Shendure et al., "Next-generation DNA sequencing," Nature Biotechnology, vol. 26, No. 10, 2008, pp. 1135-1145.

Vrana et al., "Development of a Reconstructed Cornea from Collagen-Chondroitin Sulfate Foams and Human Cell Cultures," Investigative Ophthalmology & Visual Science, vol. 49, No. 12, 2008, 7 pages.

Bieber, "Atopic Dermatitis," Ann. Dermatol., vol. 22, No. 2, pp. 25-37, 2010.

Correa et al., "Management of Patients with Atopic Dermatitis: The Role of Emollient Therapy," Dermatology Research and Practice, vol. 2012, Article 836931, 2012.

* cited by examiner

RECONSTITUTED NIPPLE SKIN MODEL

The present invention concerns a skin model that can advantageously be used to study skin rich in filaggrin and keratin, such as, for example, nipple skin or lip skin. The present invention also comprises a method for evaluating the effects of topical cosmetic, pharmaceutical or dermatological products on nipple skin, in particular on healing of nipple skin and on modulation of nipple skin inflammation, preferably using said skin model, as well as kits for implementing the method.

Nipple skin can be subject to specific dermatological lesions, called cracking. Cracking can be defined from the medical viewpoint as deep linear ulceration. It is most often associated with inflammation.

This type of lesion is found, for example, in eczema or Paget disease of the breast. Most often, however, cracking is observed in women during breastfeeding.

Nipple cracks are lesions appearing in the form of small breaks in the skin and located in female nipples. They mainly appear during the early days of breastfeeding. Most often, the cracking results from an improper position of the baby on the breast, or incorrectly latching onto the breast.

While cracking related to eczema or Paget disease of the breast require specific therapeutic treatment, cracking related to breastfeeding is benign and resolves by itself when breastfeeding is discontinued. However, cracking can be accompanied by discomfort, such as sensitive or irritated nipples, due to the inflammation present. Complications are also possible, such as mild bleeding during breastfeeding and, in rare cases, a bacterial infection.

Restoring the integrity of nipple skin is the most effective measure for preventing these discomforts. Many researchers have sought to develop effective cosmetic or therapeutic products that allow quickly relieving irritation, facilitating resorption of these cracks and, in this way, prevent any complication.

However, one of the limiting steps for identifying and characterizing these new products is evaluating their efficacy for the desired use. In order to allow rapid development of safe and effective cosmetic or therapeutic products, appropriate and predictive in-vitro models are necessary.

Many human skin models have been developed and used in predictive tests for the cosmetic or therapeutic activity of topical agents or compositions.

However, these models are not suitable for the study of the physiology and pathologies of nipple skin. This skin has specific molecular and histological features that impact its functioning.

The nipple is a specialized epidermis that has certain characteristics: it is hyperkeratinized and thickened with extended suprabasal, granular and horny layers. In comparison with "normal" skin, for example, stomach skin, nipple skin is hyperkeratinized with overexpression and specific distribution of certain markers such as filaggrin and keratin 14 (Mahler B, Cells Tissues Organs, 176(4):169-77, 2004).

In fact, it has been noted in mice that keratin 14, which is found in the basal part of keratinocytes in the stomach skin, is present in the apical part of keratinocytes in the nipple skin (Panchal et al., BMC Developmental Biology, 7:105, 2007). Increase in the level of keratin 14, and its particular distribution identifies a tissue whose cells are proliferating and which is therefore rapidly renewing. Furthermore, filaggrin is a well-known marker that confers strength and protection to the skin and plays a crucial role in the barrier function. Increase in the level of filaggrin in the nipple skin is therefore likely to play a role in its ability to heal.

Unfortunately, no model approximating nipple skin has been proposed to date.

There is still a need for a model that reproduces the characteristics of nipple skin. Therefore, there is a need for in-vitro nipple skin models, as well as in-vitro methods for testing the cosmetic or therapeutic activity of topical agents or compositions on this particular epidermis.

The inventors have developed a specialized in-vitro skin model that reproduces the biological characteristics of nipple skin, and can notably be used to screen active ingredients or even cosmetic or pharmacological formulations of interest.

The model of the invention has a particular feature of approximating the actual composition of nipple skin and comprises a large quantity of filaggrin and keratin 14 biological markers. The model of the invention comprises keratinocytes overexpressing filaggrin, and, advantageously, keratin 14. Thus, the skin model of the invention comprises special keratinocytes, which have the feature of expressing filaggrin at a higher level than what is usually observed in keratinocyte cultures. Moreover, the production of the model of the invention involves growth factors known to stimulate the expression of keratin 14.

The skin model of the invention is therefore particularly simple to implement. Moreover, it does not require using a particular commercial cell line, and has proven versatile and adaptable, provided that the keratinocytes used have the required functional characteristics.

The specific characteristics of the model of the invention allow in-vitro study of the features of nipple skin. In particular, it is possible to study the healing and inflammation processes for nipple skin from the in-vitro model of the invention, for example after having induced a lesion on the model.

The first object of the invention is a skin model characterized/specialized in that it comprises keratinocytes overexpressing filaggrin.

Thus, the skin model can be any tissue model comprising keratinocytes and in which the keratinocytes overexpress filaggrin. Thus, the skin model of the invention can be any tissue model comprising keratinocytes. The skin model of the invention is therefore not strictly limited to a particular type of tissue model, and can be adapted as needed by those skilled in the art.

"Tissue model comprising keratinocytes" means, in the sense of the invention, any in-vitro culture of skin cells comprising at least keratinocytes. Thus, the words "tissue model comprising keratinocytes" comprise single-layer keratinocyte cultures, skin cell cultures in two layers comprising keratinocytes and tissue models such as reconstructed skin cultures comprising keratinocytes. Advantageously, the skin model comprises reconstructed skin cultures comprising keratinocytes.

According to the invention, skin cells comprise at least one type of cells usually present in the hypodermis, dermis and/or epidermis. These cells thus comprise, among other things, keratinocytes, melanocytes, fibroblasts, adipocytes, endothelial cells, mastocytes, Langerhans cells and/or Merkel cells. Preferably, the skin cells according to the invention comprise at least keratinocytes and/or fibroblasts.

Single or double-layer cell cultures have been known and used for a long time, and do not require detailed description.

Moreover, many reconstructed skin models are available to those skilled in the art (who can refer, in particular, to Rosdy et al., In Vitro Toxicol., 10(1): 39-47, 1997; Ponec et al., J Invest Dermatol., 109(3): 348-355, 1997; Ponec et al., Int J Pharm., 203(1-2): 211-225, 2000; Schmalz et al., Eur J Oral Sci., 108(5): 442-448, 2000; Black et al., Tissue Eng, 11(5-6): 723-733, 2005; Dongari-Batgtzoglou and Kashleva, Nat Protoc, 1(4): 2012-2018, 2006; Bechtoille et al., Tissue Eng, 13(11): 2667-2679, 2007; Vrana et al., Invest Ophthalmol Vis Sci, 49(12): 5325-5331, 2008; Kinicoglu et al., Biomaterials, 30(32): 6418-6425, 2009; Auxenfans et al., Eur J Dermatol, 19(2): 107-113, 2009; Kinicoglu et al., Biomaterials, 32(25): 5756-5764, 2011; Costin et al., Altern Lab Anim, 39(4): 317-337, 2011; Auxenfans et al., J Tissue Eng Regen Med, 6(7): 512-518, 2012; Lequeux et al., Skin Pharmacol Physiol, 25(1): 47-55, 2012; EP 29 678; EP 285 471; EP 789 074; EP 1 451 302 B1; EP 1 878 790 B1; EP 1 974 718; US 2007/0148,771; US 2010/0,099,576; WO 02/070729; WO 2006/063864; WO 2006/063865; WO 2007/064305).

Preferably, the reconstructed skin model is selected in the group comprising epidermis models made up primarily of keratinocytes, skin models comprising a dermis and an epidermis, and skin models comprising a hypodermis, dermis and epidermis. Models comprising at least an epidermis form stratified epithelia comprising layers characteristic of the tissue considered. For example, in epidermis models, the following can be identified: a basal layer (stratum basale), a spinous layer (stratum *spinosum*), a granular layer (stratum *granulosum*), and a horny layer (stratum corneum).

Advantageously, the skin model of the invention is an epidermis model comprising a matrix support, preferably chosen from among:
  an inert support chosen from the group consisting of a semi-permeable synthetic membrane, especially a semi-permeable nitrocellulose membrane, semi-permeable nylon membrane, Teflon membrane or sponge, polycarbonate or polyethylene membrane, polypropylene, semi-permeable polyethylene terephthalate (PET) membrane, Anopore semipermeable inorganic membrane, cellulose acetate or ester (HATF), a Biopore-CM semipermeable membrane or a semi-permeable polyester membrane.
  This group includes the reconstructed Epiderm models (Skinethic®) and the EpiDerm® model, (Mattek Corporation);
  a film, a membrane or a matrix based on hyaluronic acid and/or collagen and/or fibronectin and/or fibrin.
  This group particularly includes the following models: Laserskin® (Fidia Advanced Biopolymers), Episkin® (L'Oréal).
  These models may possibly also be inoculated with fibroblasts in the dermal part.

Advantageously, pigment cells, immunocompetent cells or nerve cells can be introduced into the skin model of the invention; preferably the immunocompetent cells are Langerhans cells.

Generally, when the skin model of the invention is an epidermis model, the support matrix is produced and then inoculated with the keratinocytes of the invention to reconstruct the epidermis and finally obtain a reconstructed skin comprising keratinocytes able to overexpress filaggrin.

In the context of the invention, the term "keratinocytes" means both primary keratinocytes and immortalized keratinocytes, such as, for example, keratinocytes originating from cell lines. Keratonocyte cell lines are well known to those skilled in the art and comprise, for example, the human keratinocyte line HaCaT.

Preferably, the keratinocytes are of human origin. For example, the keratinocytes come from biological samples from a human subject.

Preferably, the keratinocytes used in the skin model are obtained in healthy subjects, regardless of their origin.

In the sense of the application, "healthy subject" means a subject with no skin diseases. Preferably, "healthy subject" means subjects with no cutaneous damage, in particular not presenting atrophy, bullae, discoloration, erythema (and exanthema), keratosis, maculae, nodules, papules, purpura, pustules, squamae, sclerosis, tumors, ulcerations, condylomata or vesicles.

In one preferred embodiment, the keratinocytes used in the skin model are obtained from healthy biological samples from a human subject.

In the sense of the application, "healthy biological samples" means biological samples with no skin damage, in particular not presenting atrophy, bullae, discoloration, erythema (and exanthema), keratosis, maculae, nodules, papules, purpura, pustules, squamae, sclerosis, tumors, ulcerations, condylomata or vesicles.

Human keratinocytes can, in particular, be isolated from skin samples, by cell culture techniques well known to those skilled in the art.

For example, the keratinocytes can be keratinocytes obtained from explant of cutaneous tissue, in particular keratinized malpighian epithelium samples. Human keratinocytes can then easily be cultured in vitro according to well-known techniques. The person skilled in the art may refer, in particular, to Leigh et al. (*Arch Dermatol Res.;* 286(1):53-61.1994).

"Explant" or "skin explant" here means a sample of cutaneous cells or tissue, which can be taken for therapeutic purposes or for testing.

In particular, an explant can be obtained during surgical excision. "Excision" here means a surgical procedure consisting of cutting (excising) a fairly wide or deep portion of the skin to treat an anomaly or growth. For example, an excision is done either to remove a cancerous or suspect tumor, or to treat a benign skin disorder which is problematic either for functional or esthetic reasons. An excision in the sense of the invention includes, for example, skin samples obtained after cosmetic surgery (breast or abdominal surgery, lifting, preputial sampling, otoplasty, i.e., ear reattachment, syndactyly or polydactyly, etc.).

An explant can also be obtained by biopsy. "Biopsy" here means a sample of cutaneous cells or tissue done for analysis purposes. Several types of biopsy procedures are known and performed in the field. The most common types include (1) incisional biopsy, in which only a sample of tissue is removed; (2) excisional biopsy (or surgical biopsy) which consists of the complete removal of a tumor mass, thereby providing a therapeutic and diagnostic procedure, and (3) needle biopsy, in which a tissue sample is removed with a needle, which may be wide or fine. There are other types of biopsy, such as, for example, smears or curettage, and these are also encompassed by the present invention.

"Immortalized keratinocytes" means, in the sense of the present application, keratinocytes that are dividing beyond the Hayflick limit. These cells have thus acquired the ability to replicate indefinitely, either following a random mutation or a deliberate modification.

It is well known that normal cells can only divide a given number of times. Once this limit is reached, the cells become senescent and then die. The Hayflick limit corresponds to the number of divisions that can be done by a normal cell, i.e., a cell can only divide a given number of times before it ceases dividing. In the sense of the present invention, the Hayflick limit corresponds to the number of divisions that can be done by a normal keratinocyte before ceasing to divide.

Keratinocytes can be immortalized following specific abnormalities, as is the case for cancerous cells, for example, or following the implementation of an immortalization technique. Immortalization techniques are well known to the person skilled in the art, who can easily choose the most suitable technique for their purpose from among them. For example, and without limiting the invention to these examples, immortalization techniques include transformation by an oncogen, in particular by the T antigen of SV40, Ras protein, Myc protein, Abl protein. Other techniques include, for example, overexpression of telomerase reverse transcriptase, for example hTERT, or culture of keratinocytes to confluence by several passes. All these techniques are conventional cell biology techniques that do not need to be detailed here.

In the sense of the present invention, the biological marker filaggrin comprises the human FLG gene (NCBI reference: Gene ID: 2312) and the products of this gene. In one particular embodiment, the filaggrin biological marker consists of the human FLG gene (NCBI reference: Gene ID: 2312). According to another embodiment, the filaggrin biological marker consists of one of the products of the human FLG gene. In the sense of the present invention, human FLG gene products comprise the human FLG gene transcript and human filaggrin protein. "Human FLG gene transcript" means, in the sense of the invention, the polynucleotide whose sequence has the NCBI reference NM_002016.1 "Human filaggrin protein" means, in the sense of the invention, the protein whose peptide sequence is the sequence with NCBI reference NP_002007.1.

"Keratinocytes overexpressing filaggrin" means, in the sense of the present invention, keratinocytes constitutively presenting an expression level of the filaggrin biological marker greater than a reference expression level.

In the sense of the invention, the reference expression level of the filaggrin biological marker is a reference level of keratinocyte expression, such as, for example, primary keratinocytes from the same species as the keratinocytes analyzed.

In the sense of the invention, the expression level of the filaggrin biological marker in keratinocytes corresponds to the quantity of human FLG gene transcripts, in particular the polynucleotide whose sequence has the NCBI reference NM_002016.1, in said keratinocytes. Preferably, the expression level of the filaggrin biological marker corresponds to the expression level of the polynucleotide whose sequence has the NCBI reference NM_002016.1.

Any technique regularly used by those skilled in the art can be implemented to measure the expression level of the filaggrin biological marker in the keratinocytes of the invention. As explained below, those skilled in the art can, in particular, use gene expression level analysis processes at the nucleotide level, such as, for example, transcriptome analysis. These methods include well-known methods such as RT-PCR or quantitative RT-PCR or even nucleic acid chips, and are detailed below.

Keratinocytes overexpressing filaggrin can easily be obtained by the person skilled in the art by conventional selection techniques regularly used in cell culture. Generally, at each cell pass regularly done according to conventional cell culture techniques, the skilled person will isolate keratinocytes in which the filaggrin level is especially high. After several passes, the skilled person will thus obtain keratinocytes overexpressing filaggrin. For further detail concerning methods for selecting keratinocytes with particular characteristics, the skilled person can refer, in particular, to Fortunel et al. (*Eur J Dermatol.*; 21 Suppl 2:12-20. 2011).

During the production of the skin model, it is possible to use, in the cell culture medium, growth factors that can induce overexpression of keratin 14. This type of growth factor is well known to those skilled in the art, and comprises, for example, fetal calf serum (FCS) and fibroblast b growth factor (bFGF). Preferentially, the culture medium for the skin model of the invention comprises at least 5% fetal calf serum, by volume relative to the total culture medium volume. In this way, the keratinocytes of the resulting skin model overexpress keratin 14.

Preferably, the skin model of the invention comprises keratinocytes overexpressing keratin 14.

"Keratinocytes overexpressing keratin 14" means, in the sense of the present invention, keratinocytes constitutively presenting an expression level of the keratin 14 biological marker greater than a reference expression level.

In the sense of the invention, the reference expression level of the biological marker keratin 14 corresponds to an average expression level for keratinocytes.

In the sense of the invention, the expression level of the keratin 14 biological marker in keratinocytes corresponds to the quantity of human KRT14 gene transcripts whose sequence has NCBI reference 3861, in particular the polynucleotide whose sequence has NCBI reference NM_000526, in said keratinocytes. Preferably, the expression level of the keratin 14 biological marker corresponds to the expression level of the polynucleotide whose sequence has the NCBI reference NM_002016.1.

Here again, any technique regularly used by those skilled in the art can be implemented to measure the level of expression of the keratin 14 biological marker in the keratinocytes of the invention.

The skin model of the invention therefore comprises special keratinocytes, which overexpress key markers, filaggrin and keratin 14, which are found in nipple skin.

The model of the invention thus permits reproducing tissues very rich in filaggrin, such as human nipple skin or lip skin. This model can then be used to study this type of tissue, or the effect of certain formulations or certain active ingredients on this type of tissue. According to one embodiment of the invention, the model of the invention is used to study nipple skin. Thus, one object of the invention is the use of a skin model according to the invention, to study nipple skin.

Moreover, the person skilled in the art can also adapt the model of the invention for specific uses. For example, the model of the invention can be modified so as to have a lesion. This type of modified model can also be used, for example, to study lesions or healing phenomena in tissues such as lip skin or nipple skin.

Thus, in one embodiment of the invention, the skin model has a lesion. Preferably, the lesion is a lesion mimicking a crack. As is well known to the skilled person, cracks can be defined from the medical viewpoint as a deep linear ulceration, possibly associated with inflammation. Cracks appear in the form of small breaks in the skin.

Thus, in the sense of the application, a lesion mimicking a crack is a lesion reproducing a linear ulceration, preferably a deep linear ulceration.

Preferably, a lesion mimicking a crack in the sense of the invention is in the form of one or more breaks in the skin model.

In order to obtain such a model, the skilled person will choose to induce a lesion in a skin model of the invention, for example mechanically. For example, the skilled person can induce a mechanical lesion simply by using a cutting object, such as a scalpel; or a superficial lesion by using any other non-cutting object that allows creating mechanical abrasion of the surface. This type of tool actually permits best reproducing the cracks observed in vivo.

Nipple skin lesions heal with difficulty during breastfeeding, and are also very inflamed, and therefore very painful. Thus, it may interesting to try to evaluate the efficacy of formulations or active ingredients on healing the injured epidermis, or even on reducing inflammation associated with the lesions. The model of the invention can thus advantageously be used in procedures for evaluating the in-vitro activity of a formulation or an active ingredient, in particular done for purposes of testing the activity of said formulation on healing nipple skin or reducing nipple skin inflammation. The model of the invention can also be used in methods for identifying a formulation or active ingredient suited for injured nipple skin, and more particularly permitting treating nipple cracks.

In particular, the inventors have identified markers involved in different aspects of healing as well as markers involved in cutaneous inflammation.

Thus, the markers selected by the inventors permit evaluating the effect of formulations on different but complementary issues associated with cutaneous lesions. The use of all of these markers allows obtaining a more complete and exhaustive evaluation of the activity of the formulation or active ingredient of interest on lesion repair, as well as reduction of nipple skin inflammation during this process.

The skin model of the invention allows observing a variation of the production of these markers, especially lactate dehydrogenase (LDH), TNFα, filaggrin, integrin β1 and TGF β1.

The methods of the invention, by using the measurement of the production level of at least one of these markers, therefore permits monitoring the effect of a formulation on nipple skin healing. Depending on the biological markers observed, the evaluation method of the invention permits not only determining if the formulation stimulates healing, but also if it contributes to reducing inflammation present in the lesions, in particular in cracks.

Cosmetic and pharmaceutical formulations and compositions comprise a large number of compounds, some of which are used to obtain a particular texture and/or viscosity. Nevertheless, these compounds can have an adverse effect on lesions, for example a proinflammatory effect. In contrast, other active ingredients can have interesting properties and have a beneficial effect on healing or inflammation processes.

The methods of the invention are thus suitable for the evaluation of the activity of isolated active ingredients. The invention thus permits precisely determining what active ingredients have an advantageous effect on nipple skin healing.

The invention has for a second object an evaluation method for the in-vitro activity of an active ingredient or formulation on nipple skin healing and/or reduction of nipple skin inflammation, characterized in that said method comprises at least the following steps:
a) contacting said active ingredient or said formulation with a skin model comprising keratinocytes overexpressing filaggrin and also comprising a lesion, such as described above;
b) measuring the production level of at least one biological marker in the skin model of step a), characterized in that said biological marker is chosen from among the group consisting of:
    epidermal integrity markers, said epidermal integrity marker being preferably lactate dehydrogenase (LDH); and
    epidermal barrier markers, said epidermal barrier marker being preferably filaggrin; and
    epidermal inflammation markers, said epidermal inflammation marker being preferably chosen from among cytokines, in particularly TNFα; and
    healing markers, said healing marker being preferably chosen from among integrins, in particular integrin β1, and TGF β1;
c) comparing the production level of at least one biological marker obtained at step b) with a reference production level;
d) evaluating the efficacy of said active ingredient or said formulation on nipple skin healing and/or reduction of nipple skin inflammation depending on the comparison of step c).

As is well known to those skilled in the art, skin healing is a natural biological phenomenon for repairing localized skin damage. This phenomenon allows the skin to recover its physical integrity after an injury.

According to one embodiment, in a first step, the active ingredient of interest is contacted with a skin model comprising keratinocytes overexpressing filaggrin and also comprising a lesion according to the invention.

Contacting the active ingredient of interest with the injured nipple skin model can be done directly, if the active ingredient formulation permits it. In some cases, it could be advantageous to formulate the active ingredient of interest, for example to obtain a liquid composition, in order to facilitate contacting it with the injured nipple skin model Thus, according to one embodiment of the invention, the process also comprises a formulation step for the active ingredient, notably in the form of a liquid solution, in particular aqueous, prior to the step of contacting said active ingredient with an injured nipple skin model.

According to another embodiment, in a first step, the formulation of interest is contacted with a skin model comprising keratinocytes overexpressing filaggrin and also comprising a lesion according to the invention. Contacting the formulation of interest with the injured nipple skin model can be done directly.

After contacting the active ingredient or formulation of interest and the skin model of the invention, the skilled person can proceed to measuring the production level of the biological markers according to the invention in the skin model thus treated.

"Biological marker" means, in the sense of the present application, a characteristic which is objectively measured and evaluated as an indicator of normal biological processes, pathogenic processes, or pharmacological responses to a therapeutic procedure. Therefore, a biological marker designates a range of substances and various parameters. For example, a biological marker can be a substance whose detection indicates a particular pathological condition (for example, the presence of activated C protein as an infection marker), or, on the contrary, a substance whose detection indicates a specific physiological condition. The biological marker according to the invention is preferably a gene, the products of a gene such as transcripts and peptides from these transcripts, a lipid, a sugar or a metabolite.

In the sense of the present invention, the biological marker is a gene, the products of a gene such as transcripts or peptides, a lipid, a sugar or a metabolite whose production changes, in particular production level, correlate with a physiological condition of nipple skin.

According to the invention, the biological marker is chosen from among epidermal integrity markers, epidermal barrier markers or epidermal inflammation markers.

According to a preferred embodiment, the epidermal integrity marker is lactate dehydrogenase (LDH).

According to the invention, the epidermal barrier marker is chosen from among filaggrin, keratins, in particular keratin 1 and keratin 10, involucrin, loricrin, transglutaminases, ceramides, cholesterol and fatty acids.

According to a preferred embodiment, the epidermal barrier marker is filaggrin.

According to the invention, the epidermal inflammation marker is chosen from among cytokines, in particular TNFα and interleukins 1, 6 and 8, leukotrienes and prostaglandins.

According to a preferred embodiment, the epidermal inflammation marker is chosen from among cytokines, in particular TNFα.

According to the invention, the healing marker is chosen from among integrins, in particular integrin β1, integrin β4, integrin α2, integrin α3, integrin α6, laminin 5, metalloproteinases, in particular metalloproteinases MMP1, MMP2 and MMP9, growth factors, in particular TGF β1 (Transforming Growth Factor B1), KGF (Keratinocyte Growth Factor), EGF (Epidermal Growth Factor), interferon gamma.

According to a preferred embodiment, the healing marker is chosen from among integrins, in particular integrin β1, and TGF β1.

These markers have been selected by the inventors because they are specifically associated with nipple skin integrity.

In healing processes, TNFα is released into the injury and promotes migration and activation of neutrophils and macrophages, which are necessary for tissue repair. However, this biological marker is a growth factor well known for its inflammatory effect. Yet, the inflammatory signal contributes to the pain felt in the case of nipple skin cracking. Thus, a reduction in the production level of TNFα at the nipple skin cracks can be correlated with a reduction in inflammation, and consequently relieve tightness due to the cracks. Variations at the production level of this marker thus permit evaluating the antiinflammatory effect of the active ingredient of interest during healing processes, and therefore the relieving effect of the active ingredient on cracking.

In the sense of the present invention, the biological marker TNFα comprises the human TNFα gene (NCBI reference: Gene ID: 7124), as well as the products of this gene. In one particular embodiment, the TNFα biological marker consists of the human TNFα gene (NCBI reference: Gene ID: 7124). According to another embodiment, the TNFα biological marker consists of one of the products of the human TNFα gene. The products of the human TNFα gene comprise the human TNFα gene transcript and the human TNFα protein. In the sense of the present invention, the human TNFα gene transcript is the polynucleotide which has the NCBI reference sequence: NM_000594. "Human TNFα protein" means, in the sense of the invention, the protein whose peptide sequence is the sequence with NCBI reference: NP_000585.

"TNFα in the peptide form" means, according to the invention, a peptide whose peptide sequence comprises the peptide sequence of human TNFα protein (NCBI reference: NP_000585).

"TNFα in the nucleotide form" means, according to the invention, at least one polynucleotide whose sequence comprises the sequence of the human TNFα gene transcript (NCBI reference: Gene ID: 7124). In the sense of the present invention, the human TNFα gene transcript is the polynucleotide which has the NCBI reference sequence: NM_000594.

LDH is an enzyme that is normally present in cell cytosol. Its presence in the media of culture cells indicates cell damage. Thus, the increase in the release of this marker is correlated with an increase in cell damage, i.e., lesions. In contrast, reduction in the release of this marker witnesses a decrease in cell damage, i.e., lesions. The reduction in the level of this marker is therefore correlated with a positive evolution in the healing process. The variations in production level of this marker allow evaluating the effect of the active ingredient of interest on healing processes, and its protective and reparative effect. Lactate dehydrogenase (LDH) is a tetrameric enzyme. In mammals, each subunit can either be type H (heart) or M (muscle). There are several LDH isotypes that differ according to the type of assembly formed by these subunits. The M subunit is encoded by the LDHA gene (NCBI reference: Gene ID: 3939), while the H subunit is encoded by the LDHB gene (NCBI reference: Gene ID: 3945). The predominant form in the skin is the LDH-2 form, which comprises three H subunits and one M subunit.

In the sense of this invention, the lactate dehydrogenase (LDH) biological marker is preferably LDH-2, which comprises three H subunits and one M subunit.

Filaggrin is a marker found in to a large extent in nipple skin cells, it is also an epidermal barrier marker. During the healing process, tissue repair is accompanied by a proliferation and differentiation of cells that come to fill the lesion in order to restore the epidermis, and therefore an increase in filaggrin production level. Increase in the production level of this marker is therefore correlated with a positive evolution of the healing process, and therefore repair of the injured tissue with restoration of an integral epidermis. The variations in production level of this marker allow evaluating the effect of the active ingredient of interest on healing processes, and its reparative effect.

"Filaggrin in its peptide form" means, according to the invention, a peptide whose peptide sequence comprises the peptide sequence of human filaggrin protein (NCBI reference: NP_002007.1).

"Filaggrin in its nucleotide form" preferably means, according to the invention, at least one polynucleotide whose sequence comprises the sequence of the human FLG gene transcript (NCBI reference: Gene ID: 2312). In the sense of the present invention, the human FLG gene transcript is the polynucleotide whose sequence has the NCBI reference NM_002016.1.

Integrin β1 is a growth factor that controls many cell functions, involved in the regulation of healing. Increase in the production level of this marker indicates amplification of the healing process and repair of injured tissue. The variations in production level of this marker allow evaluating the effect of the active ingredient of interest on healing processes, and its reparative effect.

In the sense of the present invention, the biological marker integrin β1 comprises the human ITGB1 gene (NCBI reference: Gene ID: 3688), as well as the products of this gene. In one particular embodiment, the integrin β1 biological marker consists of the human ITGB1 gene (NCBI reference: Gene ID: 3688). According to another embodiment, the integrin β1 biological marker consists of one of the products of the human ITGB1 gene. The products of the human ITGB1 gene comprise the human ITGB1 gene transcript and the human integrin β1 protein. In the sense of the present invention, the human ITGB1 transcript comprises polynucleotides whose sequence is chosen from among sequences with NCBI reference NM_002211.3, NM_133376.2 and NM_033668.2. "Human integrin β1 protein" means, in the sense of the invention, the protein whose peptide sequence is the sequence with NCBI reference: NP_002202.2, NP_596867.1 and NP_391988.1.

"Integrin β1 in the peptide form" preferably means, according to the invention, a peptide whose peptide sequence is chosen from among sequences with NCBI reference: NP_002202.2, NP_596867.1 and NP_391988.1.

"Integrin β1 in the nucleotide form" preferably means, according to the invention, at least one polynucleotide whose sequence comprises the sequence of the human ITGB1 gene transcript (NCBI reference: Gene ID: 3688). In the sense of the present invention, the human ITGB1 transcript comprises polynucleotides whose sequence is chosen from among NCBI reference sequences NM_002211.3, NM_133376.2 and NM_033668.2.

TGF β1 (for "Transforming Growth factor beta 1") is a polypeptide member of the family of beta transforming growth factors, which itself belongs to the cytokine superfamily. This peptide is particularly involved in the control of cell growth and proliferation. In the skin, and as part of the healing phenomenon, an increase in the TGF β1 production level is correlated with epidermal repair. Increase in the production level of this marker indicates amplification of the healing process and repair of injured tissue. The variations in production level of this marker allow evaluating the effect of the active ingredient of interest on healing processes, and its reparative effect.

In the sense of the present invention, the biological marker TGF β1 comprises the human TGFB1 gene (NCBI reference: Gene ID: 7040), as well as the products of this gene. In one particular embodiment, the TGF β1 biological marker consists of the human TGFB1 gene (NCBI reference: Gene ID: 7040). According to another embodiment, the TGF β1 biological marker consists of one of the products of the human TGFB1 gene. The products of the human TGFB1 gene comprise the human FLG transcript and human TGF β1 polypeptide. In the sense of the present invention, the human TGFB1 gene transcript is the polynucleotide which has the NCBI sequence reference NM_000660. Human TGF β1 polypeptide preferably means, in the sense of the invention, the polypeptide whose peptide sequence is the sequence with NCBI reference: NP_000651.

"TGF β1 in the peptide form" preferably means, according to the invention, a peptide whose peptide sequence is chosen from among sequences with NCBI reference: NP_000651.

"TGF β1 in the nucleotide form" preferably means, according to the invention, at least one polynucleotide whose sequence comprises the sequence of the human TGFB1 gene transcript (NCBI reference: Gene ID: 7040). In the sense of the present invention, the human TGFB1 gene transcript is the polynucleotide whose sequence has the NCBI reference NM_000660.

The skilled person will understand that, in the context of the invention, it is possible to select, for example, combinations of markers of a particular type. By using only one type of marker, the skilled person can obtain a precise answer on the efficacy of the formulation or active ingredient, such as, for example, a specific evaluation of the efficacy on epidermal inflammation or a specific evaluation of the efficacy on healing. The skilled person could then use, for example, combinations of markers consisting of epidermal integrity markers, combinations of markers consisting of epidermal barrier markers, combinations of markers consisting of epidermal inflammation markers, combinations of markers consisting of healing markers.

It will then be obvious to the skilled person that the method of the invention will permit evaluating the efficacy of the formulation or active ingredient more complete if a great number of different types of markers are used. The skilled person will be able, for example, to evaluate both the efficacy of the formulation or active ingredient on epidermal inflammation and on healing.

Other types of marker combinations can also be envisaged, such as, for example, combinations to two types of markers, such as:

combinations of markers consisting of epidermal integrity markers and epidermal barrier markers, in particular the combination of markers consisting of lactate dehydrogenase (LDH) and filaggrin;

combinations of markers consisting of epidermal integrity markers and epidermal inflammation markers, in particular the combination of markers consisting of lactate dehydrogenase (LDH) and TNFα;

combinations of markers consisting of epidermal integrity markers and healing markers, in particular the combination of markers consisting of lactate dehydrogenase (LDH) and integrin β1 or the combination of markers consisting of lactate dehydrogenase (LDH) and TGF β1;

combinations of markers consisting of epidermal barrier markers and epidermal inflammation markers, in particular the combination of markers consisting of filaggrin and TNFα.

combinations of markers consisting of epidermal barrier markers and healing markers, in particular the combination of markers consisting of filaggrin and integrin β1 or the combination of markers consisting of filaggrin and TGF β1; or combinations of markers consisting of epidermal inflammation markers and healing markers, in particular the combination of markers consisting of TNFα and integrin β1 or the combination of markers consisting of TNFα and TGF β1.

Advantageously, the skilled person will be able to use combinations of three types of markers, such as:

combinations of markers consisting of epidermal integrity markers, epidermal barrier markers and epidermal inflammation markers, in particular the combination of markers consisting of lactate dehydrogenase (LDH), filaggrin and TNFα;

combinations of markers consisting of epidermal integrity markers, epidermal barrier markers and healing markers, in particular the combination of markers consisting of lactate dehydrogenase (LDH), filaggrin and TGF β1 or the combination of markers consisting of lactate dehydrogenase (LDH), filaggrin and integrin β1;

combinations of markers consisting of epidermal integrity markers, epidermal inflammation markers and healing markers, in particular the combination of markers consisting of lactate dehydrogenase (LDH), TNFα and TGF β1 or the combination of markers consisting of lactate dehydrogenase (LDH) and TNFα and integrin β1;

combinations of markers consisting of epidermal barrier markers, epidermal inflammation markers and healing markers, in particular the combination of markers consisting of filaggrin, TNFα and TGF β1 or the combination of markers consisting of filaggrin, TNFα and integrin β1.

According to a preferred embodiment, step b) comprises measuring the production level of a combination of biological markers consisting of lactate dehydrogenase (LDH), TNFα, filaggrin, integrin β1 and TGF β1.

Thus, the biological marker according to the invention can be a gene, or a gene product with a particular activity, such as an enzymatic activity, for example.

For each of these types of markers, many methods are available to the skilled person to measure the production level of said biological marker. According to the type of marker used, the terms "production level" may refer to different variables, which depend on the nature of the marker examined.

For example, when the biological marker is a gene, the terms "production level of the biological marker" generally refer to the level of synthesis of at least one of the products of this gene. More precisely, when the biological marker is a gene, the production level of said biological marker is the quantity or concentration of at least one of the transcripts of said gene or at least one of the various isoforms of the proteins resulting from said transcripts.

When the marker is the product of a gene with an enzymatic activity, the terms "production level of the biological marker" preferably refer to the enzymatic activity level of said marker. In the sense of the present invention, the enzymatic activity of said marker is the quantity of substrate for said marker catalyzed per unit of time by means of a defined quantum of said marker. Enzymatic activity unit U is conventionally expressed in μmol/min or in kat (mol/s). Enzymatic activity U can also be expressed in mg/min when the substrate for the enzyme exists in the body in the polymer form, as is the case, for example, when the substrate is chosen from among sugars or glycosaminoglucans.

The skilled person, seeking to determine if one of the gene products of interest has an enzymatic activity, will easily consult the relevant scientific literature or refer to public databases such as, for example, those collected on the ExPASy website, which notably lists enzymes (http://enzyme.expasy.org).

According to a preferred embodiment of the invention, the LDH biological marker is the product of a gene with enzymatic activity.

To measure the enzymatic activity level of a marker, the skilled person could use any technique well known in the art. In particular, the enzymatic activity of the LDH enzyme can be measured by an enzymatic test: released LDH reduces NAD+ to NADH+H+ by oxidation of lactate into pyruvate, in a second step, a catalyst (diaphorase) transfers 2H from NADH+H+ to tetrazolium salt INT which is then reduced to formazan. The formation of formazan is shown by the induction of a stain measured by colorimetry. The quantity of formazan formed is directly correlated with the enzymatic activity of LDH in the supernatant. For example, the enzymatic activity of the LDH enzyme can be measured with a colorimetric test based on the detection of formazan salts using a commercial kit (for example cytotoxicity detection kit-LDH, Roche).

"Measuring the production level of a combination of biological markers" means, in the sense of this application, measuring the production level of each of the markers of the combination. The production of a gene can be measured, for example, at the nucleotide level, by measuring the quantity of transcripts for said gene and their variants, and can also be measured, for example, at the peptide level, by measuring, for example, the quantity of one or more isoforms of the proteins resulting from said transcripts and their variants. Thus, "measuring the production level of said gene" means, in the sense of the invention, measuring the quantity of gene product in the peptide form or in the nucleotide form.

In this case, the process of the invention can comprise one or more prior steps before measuring the production of the biological marker, said steps corresponding to extraction from the nipple skin model of step a) of an mRNA sample (or the corresponding cDNA sample) or a protein sample. This can then be directly used to measure marker production. Preparation or extraction of mRNA (as well as reverse transcription of this mRNA into cDNA) or proteins from a tissue such as a skin model or cells are routine procedures well known to the skilled person.

According to a preferred embodiment of the invention, the production level of the marker chosen from among LDH, TNFα, TGFβ1 and filaggrin corresponds to the production level of said marker in the nucleotide form. According to a preferred embodiment of the invention, the production level of the integrin β1 marker corresponds to the production level of said marker in the peptide form.

For each of these types of biological markers of the invention, many methods are available to the skilled person to measure the production level of said biological marker.

When the biological marker is a gene, and when the production level of the marker is measured at the nucleotide level, i.e., by measuring the quantity of the gene product in its nucleotide form, any technology regularly used by the skilled person can be implemented. Analysis methods for gene production level at the nucleotide level, such as, for example, analysis of the transcriptome, include well-known methods such as RT-PCR or quantitative RT-PCR or even nucleic acid chips. "Nucleic acid chips" here means several different nucleic acid probes that are attached to a substrate, which can be a microchip, a glass slide or a microsphere. The microchip can be made up of polymers, plastics, resins, polysaccharides, silica or a silica based material, carbon, metals, inorganic glass or nitrocellulose. The probes can be nucleic acids such as cDNAs (cDNA chip), mRNAs (mRNA chip) or oligonucleotides (oligonucleotide chip); said oligonucleotides can typically have a length comprised between approximately 25 and 60 nucleotides. To determine the production profile of a particular gene, a nucleic acid corresponding to all or part of the gene is labeled and then contacted with the chip under hybridization conditions, leading to the formation of complexes between said labeled target nucleic acid and the probes attached to the surface of the chip which are complementary to this nucleic acid. The presence of labeled hybridized complexes is then detected.

Preferably, the invention is implemented by using any current or future method that allows determining the production of genes on the basis of the quantity of mRNA in the sample. For example, the skilled person can measure the production of a gene by hybridization with a labeled nucleic acid probe, such as by northern blot (for mRNA) or by Southern blot (for cDNA), as well as by techniques such as the serial analysis of gene expression (SAGE) method and its derivatives, such as longSAGE, superSAGE, deepSAGE, etc. It is also possible to use tissue chips (also known as TMAs: tissue microarrays). The tests usually used with tissue chips comprise immunohistochemistry and fluorescent in-situ hybridization. For mRNA analysis, tissue chips can be paired with fluorescent in-situ hybridization. Finally, it is possible to use massively parallel sequencing to determine the quantity of mRNA in the sample (RNA-Seq or whole transcriptome shotgun sequencing). For this purpose, several massive parallel sequencing methods are available. Such methods are described, for example, in U.S. Pat. No. 4,882,127, U.S. Pat. No. 4,849,077; U.S. Pat. No. 7,556,922; U.S. Pat. No. 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure Et Ji, Nat Biotechnol., 26(10): 1135-45. 2008; Pihlak et al., Nat Biotechnol., 26(6): 676-684, 2008; Fuller et al., Nature Biotechnol., 27(11): 1013-1023, 2009; Mardis, Genome Med., 1(4): 40, 2009; Metzker, Nature Rev. Genet., 11(1): 31-46, 2010.

Moreover, any method to determine the production level of a polypeptide known to the skilled person can be used. The methods for determining the production level of a polypeptide include, for example, mass spectrometry, biochemical tests, including immunoassays such as, for example, conventional detection immunoassays (ELISA and ELISPOTS), or alternatively, for example immunoassays employing transfer techniques on carrier proteins, such as slot blot (also called dot blot) or western blot. For example, it is possible to use protein chips, antibody chips or tissue chips combined with immunohistochemistry. Other techniques which may be used are comprised of FRET or BRET techniques, microscopy and histochemistry methods, including confocal microscopy and electron microscopy methods, methods based on the use of one or more excitation wavelengths and a suitable optical method, such as an electrochemical method (voltammetry techniques and amperometry), the atomic force microscope, and radiofrequency methods, such as multipolar resonance spectroscopy, confocal and non-confocal, fluorescence detection, luminescence, chemiluminescence, absorbance, reflectance, transmittance, birefringence or refractive index (for example, surface plasmon resonance, by ellipsometry, by resonant mirror method, etc.), flow cytometry, radioisotope or magnetic resonance imaging, polyacrylamide gel electrophoresis (SDS-PAGE); by HPLC-mass spectrometry, liquid chromatography/tandem mass spectrometry (LC-MS/MS). All these techniques are well known to the skilled person and it is not necessary to detail them here.

By "reference production level of a biological marker" is meant, in the sense of the present application, any production level for said marker used as a reference. For example, a reference production level can be obtained by measuring the production level of the marker of interest in a nipple skin model under specific conditions. The skilled person will know to choose these specific conditions so as to serve their objective in implementing the invention.

Thus, according to a preferred embodiment, the reference production level of a biological marker is the production level of said marker obtained in an injured nipple skin model not treated with the formulation of interest.

According to another preferred embodiment, the reference production level of a biological marker is the production level of said marker obtained in a nipple skin model contacted with a reference formulation.

Preferably, the reference formulation is chosen from among the list made up of formulations conventionally used in dermatology or cosmetics, in particular formulations comprising active ingredients such as antiinflammatories/ anti-irritants or healing and restructuring agents of the skin barrier.

Antiinflammatory/anti-irritant agents used in dermatology and cosmetics are well-known to the skilled person. Generally, they limit the inflammatory reaction conducted via cytokines or arachidonic acid metabolism mediators and have soothing and anti-irritant properties. The anti-inflammatories/anti-irritants that can be included in a reference formulation in the sense of the invention are glycyrrhetinic acid (licorice derivatives) with its salts and esters, lipoic acid, beta-carotene, vitamin B3 (niacinamide, niacinamide), vitamin E, vitamin C, vitamin B12, flavonoids (green tea, quercetin, etc.), lycopene and lutein, avocado sugars, avocado oil distillate, arabinogalactan, lupin peptides, a lupin total extract, a quinoa peptide extract, Cyloceramide (oxazoline derivative), isoflavones such as genistein/genistin, daidzein/daidzin, spring water or thermal water (Avene water, La Roche Posay water, Saint Gervais water, Uriage water, Gamarde water), goji berry extracts (*Lycium barbarum*), peptides or complexes of plant amino acids or topical dapsone, or steroidal anti-inflammatory drugs (AIDs), such as corticosteroids or non-steroidal drugs (NSAIDs).

Cutaneous barrier healing and restructuring agents used in dermatology and cosmetics are well-known to the skilled person. Generally, they stimulate synthesis of key epidermal lipids. Skin barrier healing and restructuring agents that can be included in a reference formulation in the sense of the invention are vitamin A, panthenol (vitamin B5), avocado sugars, sunflower oil distillate, lupeol, maca peptide extract, quinoa peptide extract, arabinogalactan, zinc oxide, magnesium, silicon, madecassic or asiatic acid, dextran sulfate, coenzyme Q10, glucosamine and its derivatives, chondroitin sulfate and generally glycosaminoglycans or GAGs, dextran sulfate, ceramides, cholesterol, squalane, phospholipids, peptides from fermented or unfermented soybean, plant peptides, marine, plant or biotechnological polysaccharides such as algae or fern extracts, trace elements, tannin plant extracts such as tannins derived from gallic acid called gallic or hydrolysable tannins, originally found in oak gall, and catechin tannins resulting the polymerization of flavanic units for which the *catechu* (*Acacia catechu*) provides a model. Minerals that can be used are advantageously chosen from among the group made up of copper, magnesium, manganese, chromium, selenium, silicon, zinc and their mixtures. Sunflower concentrates can also be used, more advantageously linoleic sunflower concentrates such as the active ingredient sold by Laboratoires Expanscience, Soline, plant oil unsaponifiables, such as Avocadofurane® or PPAR agonists (rosiglitazone, pioglitazone), RXR and LXR.

The skilled person could also use as a reference formulation any known formulation of the prior art, and especially any formulation known for its healing and/or antiinflammatory properties.

The following compositions can be named as examples:
avocado sugars such as described in application WO 2005/115421. This composition is especially suited for treatment of skin barrier repair and inflammation;
avocado peptides such as described in application WO2005/105123. This composition is especially suited for treatment of irritation and inflammation;
avocado oil such as described in applications WO2004/012496, WO2004/012752, WO2004/016106, WO2007/057439);
avocado furans, such as can be obtained by the method described in WO 01/21605. This composition, also sold under the trademark Avocadofurane® is particularly suited for the treatment of inflammation, and can improve healing.
5 alpha Avocuta® (butyl avocadate);
avocado and soy unsaponifiables. The avocado and soy unsaponifiables that can be used in combination are advantageously a mixture of furanic avocado unsaponifiables and soy unsaponifiables, in a respective ratio of approximately 1:3 to 2:3. The avocado and soy unsaponifiables are even more advantageously the product Piasclédine® sold by Laboratoires Expanscience;

Sunflower oil distillate, even more advantageously with linoleic sunflower concentrates, such as the active ingredient sold by Laboratoires Expanscience, Soline® (described in particular in application WO 01/21150). This composition is especially suited for inflammation treatment and skin barrier repair.

Soy unsaponifiable, such as obtained in the produce described according to international application WO01/51596;

Lupeol (FR 2 822 821, FR 2 857 596). This composition is especially suited to promote healing;

lupin peptides such as described in application WO2005/102259. This composition is especially suited for treatment of inflammation;

lupin total extract (such as described in WO2005/102259). This composition is particularly suited for the treatment of irritations;

lupin oil, advantageously a sweet white lupin oil such as described in international application WO 98/47479;

maca peptide extract (in particular such as descried in application WO2004/112742).

This composition is particularly appreciated for its healing properties;

rice peptides (see application WO 2008/009709);

Cycloceramide® (oxazoline derivative) such as described in applications WO2004050052, WO2004050079, and WO2004112741. This composition is particularly suited for the treatment of inflammatory reactions;

quinoa extract, in particular such as descried in application WO2008/080974. This composition is especially suited for treatment of inflammatory conditions and skin barrier repair.

Cupuaçu butter. This composition is particularly appreciated for its moisturizing properties;

Finally, the skilled person will be able to use as a reference formulation any formulation of the prior art known for its effect on nipple skin, such as, for example, a balm whose composition can be such as described more specifically in the experimental part of this application. Other reference formulations well known in the domain of nipple skin cracks are breast milk, whose application on cracks is recommended to facilitate healing, glycerin and lanolin.

The skilled person will also easily understand that the comparison of step c) is preferably done between production level measurements obtained for nipple skin models with similar or even identical histological compositions. "Similar histological compositions" means, in the sense of the present application, that the relative proportions of the cell types comprised in the nipple skin models compared are similar. Thus, it is preferable that the relative proportions of cell types comprised in the nipple skin model of step a) differ by no more than 5% of the relative proportions of the cell types comprised in the nipple skin model used for obtaining the reference production level of step c). "Relative proportion of a cell type" means, in the sense of the present application, the ratio of the number of cells corresponding to this cell type to the total number of cells comprised in the skin model. Thus, it is preferable, for example, that the proportion of keratinocytes to the total number of cells in the nipple skin model of step a) not differ by more than 5% of the proportion of keratinocytes over the total number of cells in the nipple skin model used to obtain the reference production level of step c). "Identical histological compositions" means, in the sense of the present application, that the relative proportions of the cell types comprised in the nipple skin models compared are identical. Thus, it is preferable that the relative proportions of cell types comprised in the nipple skin model of step a) are identical to the relative proportions of the cell types comprised in the nipple skin model used for obtaining the reference production level of step c) when they do not differ by more than 0.1%. Advantageously, the proportion of keratinocytes to the total number of cells in the nipple skin model of step a) does not differ by more than 0.1% of the proportion of keratinocytes over the total number of cells in the nipple skin model used to obtain the reference production level of step c).

The skilled person will also easily understand that the comparison of step c) is preferably done between production level measurements obtained for nipple skin models of similar or even identical size, volume or weight. In the sense of the present invention, it is preferable that the size, volume or weight of the nipple skin model of step a) not differ by more than 5% of the size and/or volume and/or weight of the nipple skin model used for obtaining the reference production level of step c). Thus, it is preferable that the size, volume or weight of the nipple skin model of step a) not differ by more than 5% of the size, volume or weight of the nipple skin model used for obtaining the reference production level of step c). More preferably, the size, volume or weight of the nipple skin model of step a) does not differ by more than 5% of the size, volume or weight of the nipple skin model used for obtaining the reference production level of step c). Even more preferably, the size, volume or weight of the nipple skin model of step a) does not differ by more than 0.1% of the size, volume or weight of the nipple skin model used for obtaining the reference production level of step c). Alternatively, if the skin models differ by more than 5% of the size, volume and weight, the skilled person could normalize the level obtained in step b) and the reference level obtained in step c) with a normalization factor.

This normalization factor could be, for example, a directly accessible physical marker such as the mass of cells in the sample, or the mass of a cell constituent, such as the mass of cellular DNA or the mass of cellular proteins.

It may also be advantageous to use as a normalization factor the production level of a gene that is expressed at the same level in all or nearly all the cells of the body. In other words, according to a particular embodiment of the present invention, the production level of a housekeeping gene is used as a normalization factor. According to another embodiment, the level obtained in step b) and the reference level of step c) are normalized by using the production level, not of housekeeping genes, but of proteins encoded by these genes. A housekeeping gene is a gene expressed in all cell types, which encodes a protein with a basic function necessary for the survival of all cell types. A list of human housekeeping genes can be found in Eisenberg et al. (Trends in Genetics 19: 362-365, 2003). For example, housekeeping genes of the invention include B2M, TFRC, YWHAZ, RPLO, 18S, GUSB, UBC, TBP, GAPDH, PPIA, POLR2A, ACTB, PGK1, HPRT1, IPO8 and HMBS.

The skilled person could also easily evaluate the efficacy of the formulation of interest according to the comparison of step c).

For example, when the production level of LDH measured in step b) is less than or equal to the production level of these markers obtained in an injured nipple skin model not treated with the formulation of interest, then the formulation is effective on nipple skin healing.

For example, when the production level of TNFα measured in step b) is less than or equal to the production level of these markers obtained in an injured nipple skin model not treated with the formulation of interest, then the formulation is effective on nipple skin inflammation.

According to another example, when the production level of integrin β1 measured in step b) is greater than or equal to the production level of these markers obtained in an injured nipple skin model not treated with the formulation of interest, then the formulation is effective on nipple skin healing and/or inflammation.

According to another example, when the production level of filaggrin measured in step b) is greater than or equal to the production level of these markers obtained in an injured nipple skin model not treated with the formulation of interest, then the formulation is effective on nipple skin healing and/or inflammation.

According to another example, when the production level of TGF β1 measured in step b) is greater than or equal to the production level of these markers obtained in an injured nipple skin model not treated with the formulation of interest, then the formulation of interest is effective on nipple skin healing and/or inflammation.

According to another example, when the production level of LDH measured in step b) is less than or equal to the production level of these markers obtained in an injured nipple skin model contacted with a reference formulation, then the formulation of interest is more effective on nipple skin healing than the reference formulation.

According to another example, when the production level of TNFα measured in step b) is less than or equal to the production level of these markers obtained in an injured nipple skin model contacted with a reference formulation, then the formulation of interest is more effective on nipple skin healing than the reference formulation.

According to another example, when the production level of integrin β1 measured in step b) is greater than or equal to the production level of these markers obtained in an injured nipple skin model contacted with a reference formulation, then the formulation of interest is more effective on nipple skin healing than the reference formulation.

According to another example, when the production level of filaggrin measured in step b) is greater than or equal to the production level of these markers obtained in an injured nipple skin model contacted with a reference formulation, then the formulation of interest is more effective on nipple skin healing than the reference formulation.

According to another example, when the production level of TGF β1 measured in step b) is greater than or equal to the production level of these markers obtained in an injured nipple skin model contacted with a reference formulation, then the formulation of interest is more effective on nipple skin healing than the reference formulation.

In another aspect, the invention allows to isolate active ingredients or formulations with an effect on nipple skin and, more advantageously, when this skin is injured. The invention therefore permits identifying active ingredients or formulations to treat nipple skin lesions, in particular cracks.

The invention therefore has for an object a method for identifying an active ingredient or a formulation for treating nipple skin lesions, in particular cracks, said process comprising the following steps:
a) contacting a candidate active ingredient or a candidate formulation with a skin model comprising keratinocytes overexpressing filaggrin and also comprising a lesion, such as described above;
b) measuring the production level of at least one biological marker in the nipple skin model of step a), characterized in that said biological marker is chosen from among the group consisting of:
  epidermal integrity markers, said epidermal integrity marker being preferably lactate dehydrogenase (LDH); and
  epidermal barrier markers, said epidermal barrier marker being preferably filaggrin; and
  epidermal inflammation markers, said epidermal inflammation marker being preferably chosen from among cytokines, in particularly TNFα; and
  healing markers, said healing marker being preferably chosen from among integrins, in particular integrin β1, and TGF β1;
c) comparing the production level of at least one biological marker obtained at step b) with a reference production level;
d) determining if said candidate active ingredient or said candidate formulation is a formulation to treat nipple skin lesions, in particular cracks, according to the comparison of step c).

The candidate active ingredient or the candidate formulation is an active ingredient or formulation to treat nipple skin lesions, in particular cracks, if said candidate active ingredient or said candidate formulation modulates the production of at least one biological marker of the invention. This modulation can be, as applicable, and in particular depending on the nature of the biological marker, an increase or decrease in the production of said marker. In particular, it may be interesting to isolate active ingredients or formulations stimulating the production of markers correlated with improved healing or even formulations reducing inflammation.

The invention therefore allows to identify raw materials improving healing and reducing inflammation. The identification of biological markers according to the invention consequently permits identifying whether or not raw materials modulate the production of these markers.

In another aspect, the invention allows to isolate the raw material that can be used in the development of formulations appropriate for nipple skin.

The invention therefore has for an object a method for identifying a raw material that can be used for the preparation of a formulation for treating nipple skin lesions, in particular cracks, said process comprising the following steps:
a) contacting a candidate raw material with a skin model comprising keratinocytes overexpressing filaggrin and also comprising a lesion, such as described above;
b) measuring the production level of at least one biological marker in the nipple skin model of step a), characterized in that said biological marker is chosen from among the group consisting of:
  epidermal integrity markers, said epidermal integrity marker being preferably lactate dehydrogenase (LDH); and
  epidermal barrier markers, said epidermal barrier marker being preferably filaggrin; and
  epidermal inflammation markers, said epidermal inflammation marker being preferably chosen from among cytokines, in particularly TNFα; and
  healing markers, said healing marker being preferably chosen from among integrins, in particular integrin β1, and TGF β1;
c) comparing the production level of at least one biological marker obtained at step b) with a reference production level;
d) determining if said candidate raw material is a raw material for the preparation of a formulation to treat nipple skin lesions, in particular cracks, according to the comparison of step c).

According to a preferred embodiment, step b) comprises measuring the production level of a combination of biological markers consisting of lactate dehydrogenase (LDH), TNFα, filaggrin, integrin β1 and/or TGF β1. In other words, step b) comprises measuring the production level of each of the biological markers of a combination of biological markers consisting of lactate dehydrogenase (LDH), TNFα, filaggrin, integrin β1 and/or TGF β1.

It is clear that the invention also permits evaluating the safety of certain active ingredients or certain formulations, or even identifying among these active ingredients or these formulations those that have optimal safety qualities with regard to injured nipple skin. Active ingredients or formulations are believed to have safe qualities if they are not detrimental to human health when they are applied under normal or reasonably predictable conditions of use. The skilled person will understand easily that it is sufficient just to measure the production of one or more biological markers according to the invention to determine if a formulation can be used on injured nipple skin.

The invention has for another object a kit for implementing a method according to the invention, comprising the means necessary for measuring the production level of at least one biological marker chosen from among the group consisting of:
  epidermal integrity markers, said epidermal integrity marker being preferably lactate dehydrogenase (LDH); and
  epidermal barrier markers, said epidermal barrier marker being preferably filaggrin; and
  epidermal inflammation markers, said epidermal inflammation marker being preferably chosen from among cytokines, in particularly TNFα; and
  healing markers, said healing marker being preferably chosen from among integrins, in particular integrin β1, and TGF β1;

According to one particular embodiment, the kit according to the invention comprises the means necessary for measuring the production level of each of the biological markers of the combination consisting of LDH, TNFα, filaggrin, integrin β1 and/or TGF β1

Preferentially, the means necessary for measuring the production level of integrin β1 are antibodies specific for said markers.

Preferably, the means necessary for measuring the production level of TNFα, filaggrin and TGF β1 comprise nucleic probes and/or amplification primers that can bind to at least one of these biological markers in its nucleotide form.

The following examples are provided here for illustration purposes and are not intended to be limiting, unless otherwise indicated.

LEGEND OF THE FIGURES

FIG. 1: Histology of a reconstructed epidermis (on day 17) obtained from the batch of keratinocytes chosen for implementing the nipple model.

Figure 2:
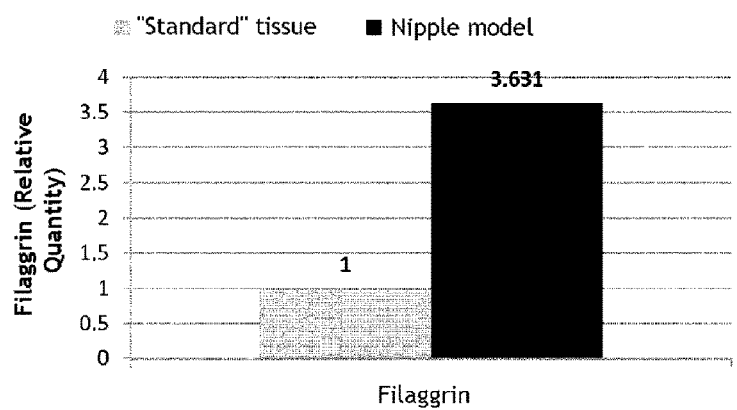

FIG. 2: Gene expression of filaggrin in the reconstructed skin after 24 hours of incubation FIG. 3: Release of LDH into the culture medium 4 hours and 24 hours after injuring the reconstructed nipple skin FIG. 4: Gene expression of TNFα in the reconstructed nipple skin 4 hours after injury FIG. 5: Gene expression of filaggrin in the reconstructed nipple skin 24 hours after injury FIG. 6: Analysis of the production of integrin β1 by western blot in the reconstructed nipple skin 24 hours after injury FIG. 7: Release of LDH into the culture medium 4 hours after injuring the reconstructed nipple epidermis FIG. 8: Gene expression of TNFα in the reconstructed nipple epidermis 24 hours after injury FIG. 9: Gene expression of TGF β1 into the reconstructed nipple epidermis 24 hours after injury FIG. 10: Labeling of integrin β1 in reconstructed nipple epidermis 4 hours after injury (blue=nucleus, dapi; red=integrin)

Figure 11:
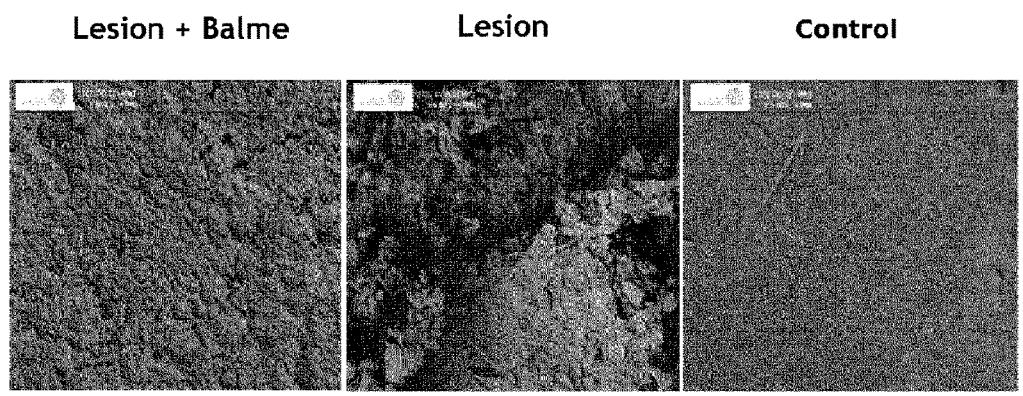

FIG. 11: Scanning electron microscopy (SEM) imaging of the reconstructed nipple epidermal surface 4 hours after injury (magnification×1000)

EXAMPLES

Example 1: Development of a Nipple Tissue Model for Evaluating a Breastfeeding Balm Objectives: Development of a model mimicking the characteristics and morphology of nipple epithelium to implement an experimental model mimicking fissures and cracks to evaluate the efficacy of cosmetic products as soothing (antiinflammatory) and repair treatment.

The nipple is a specialized epidermis that has certain characteristics: it is hyperkeratinized and thickened with extended suprabasal, granular and horny layers.

At the molecular level, there is increased production and a specific distribution of certain markers (high level of production in multiple layers of the epidermis): filaggrin (barrier marker→different tissue response to external stimuli) and keratin 14 (mitosis marker, indicative of a hyperproliferative state of the tissue).

The nipple model was obtained by reconstruction of an epidermis or complete skin (reconstructed epidermis on a collagen matrix) from a batch of keratinocytes overexpressing filaggrin.

A. Selection of the Keratinocyte Batch to be Used to Produce the Nipple Model

Reconstructed epidermises were produced from different batches of keratinocytes and analyzed comparatively by histochemistry and immunohistochemistry.

The batch chosen to produce the nipple model is a batch of keratinocytes overexpressing filaggrin, and after reconstruction of an epidermis, having a large number of granular layers with many keratohyalin granules and extensive labeling of filaggrin.

This keratinocyte batch was used in the following steps to produce tissue models mimicking the nipple.

A slice of a reconstructed epidermis (on day 17) obtained from the batch of keratinocytes chosen for implementing the nipple model is illustrated in FIG. 1.

B. Characterization of a Nipple Model
1. Materials and Methods

The nipple model was obtained by reconstruction of skin (from the batch of keratinocytes defined previously), on a collagen matrix containing fibroblasts.

At the same time, a standard skin was reconstructed under the same conditions, on a collagen matrix containing fibroblasts, from a batch of standard keratinocytes (not overexpressing filaggrin). This standard tissue serves as a reference for the nipple tissue model.

The reconstructed tissues were incubated for 4 hours and 24 hours and then the gene expression of filaggrin was studied by real-time quantitative PCR (qPCR).

The reconstructed skins were lysed and the total RNAs extracted and then reverse transcribed into cDNA. The expression of the gene of interest (filaggrin) was analyzed by real-time qPCR and compared to the expression of housekeeping gene GAPDH.

2. Results

The nipple skin model expresses much more filaggrin than a standard skin model (+260%). These results are illustrated by FIG. 2. They confirm that the model implemented approximates nipple physiology in terms of filaggrin production.

C. Study 1: Use of a Reconstructed Nipple Skin Model to Evaluate the Reparative and Antiinflammatory Efficacy of a Breastfeeding Balm 1. Materials and Methods The nipple model was obtained by reconstruction of skin from a batch of keratinocytes overexpressing filaggrin (as described previously), on a collagen matrix containing fibroblasts.

A lesion (mechanical wound) was created on the surface of the skin in order to mimic a nipple crack or fissure. The test product (breastfeeding balm) was applied topically immediately after creating the injury. Any balm formulation could be tested by the method of the invention, such as, for example, formulations 1-3 below.

The results presented below are those obtained for the balm whose composition corresponds to formulation 3 ("breastfeeding balm 3").

Breastfeeding Balm 1

| Raw material/Brand name | % |
|---|---|
| PURIFIED WATER | From 5 to 20% |
| STARCH | From 5 to 20% |
| GLYCEROL | QS 100% |
| BUTTER or OIL | From 5 to 20% |
| LANOLIN | QS 100% |

Breastfeeding Balm 2
Breastfeeding Balm 3

| Raw material/Brand name | % |
|---|---|
| PURIFIED WATER | QS 100% |
| SHEA BUTTER | From 5 to 20% |
| GLYCEROL | From 5 to 20% |
| DECYL PENTANOATE | From 5 to 20% |
| FATTY PHASE GELLING AGENT | From 1 to 5% |
| METHYLGLUCOSEDIOLATE | From 1 to 5% |
| PRESERVATIVE SYSTEM | From 1 to 5% |
| VEGETABLE WAX | From 1 to 5% |
| ACTIVE INGREDIENTS | From 1 to 5% |
| EMULSIFIER | From 1 to 5% |
| XANTHAN GUM | From 0 to 1% |
| pH ADJUSTER | From 0 to 1% |
| ANTIOXIDANT | From 0 to 1% |

The reconstructed skin was then incubated for 4 hours and 24 hours and then the following parameters were analyzed:
Release of LDH,
Gene expression (real-time qPCR) of TNFα and filaggrin,
Integrin β1 production (western blot).

a. Quantification of Released LDH:

The LDH released into the reconstructed skin culture medium was quantified by means of a colorimetric test based on the detection of formazan salts whose formation is related to the enzymatic activity of the enzyme. The quantity of LDH was determined using a standard curve and expressed in mU/ml.

b. Real-Time qPCR:

The reconstructed skins were lysed and the total RNAs extracted and then reverse transcribed into cDNA. The expression of the genes of interest (TNFα, filaggrin) was analyzed by real-time qPCR and compared to the expression of housekeeping gene GAPDH.

c. Analysis of Integrin β1 by Western Blot:

The reconstructed skins were lysed in the presence of protease inhibitors. The proteins resulting from samples were quantified, separated by polyacrylamide gel electrophoresis and then transferred onto a nitrocellulose membrane. The membranes were then incubated in the presence of a primary anti-integrin β1 antibody (Santa Cruz), and then in the presence of a labeled secondary antibody (Invitrogen). The chemiluminescence signal was then displayed and quantified; its intensity is proportional to the quantity of integrin β1 produced.

2. Results a. Evaluation of the Cell Membrane Integrity: LDH Assay

Figure 3:
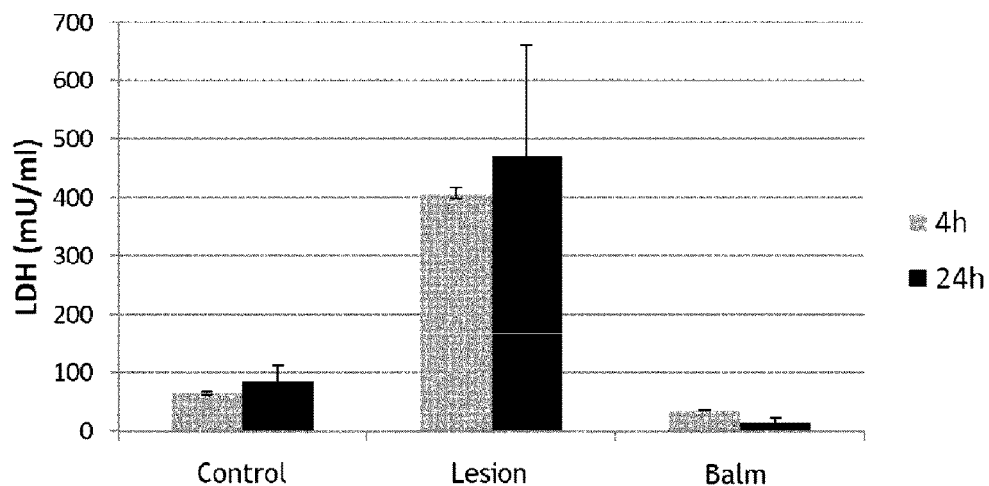

The LDH assay results are indicated in Table 1 and illustrated by FIG. 3.

TABLE 1

| | LDH (mU/ml) | | | |
|---|---|---|---|---|
| | 4 hours | | 24 hours | |
| Control tissue | 64 ± 2.99 | | 86.5 ± 24.74 | |
| Injured tissue | 407 ± 9 | +536% | 470.5 ± 191.62 | +444% |
| Injured tissue + balm | 35 ± 0.86 | −91% | 14.5 ± 7.78 | −97% |

Cell membranes form a functional membrane around cells. When cells are damaged, the membranes are altered and become porous and permeable to certain components.

Cell membrane integrity was evaluated by measurement of LDH (lactate dehydrogenase) in the extracellular medium. This enzyme is normally present in the cytosol and is undetectable in the extracellular space in the absence of cell damage.

The reconstructed skin lesion induced extensive release of LDH into the extracellular space, bearing witness to the impaired integrity of the cell membranes. Topical application of the breastfeeding balm greatly reduced LDH release. The breastfeeding balm protects tissue integrity and accelerates repair thereof after the injury.

b. Evaluation of the Inflammatory Response: Expression of TNFα

Figure 4:
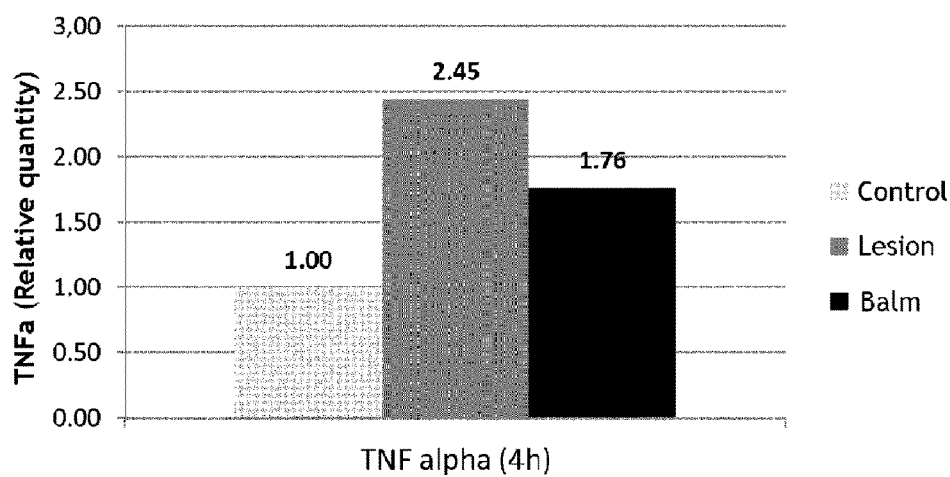

The TNFα expression measurement results are indicated in Table 2 and illustrated by FIG. 4.

TABLE 1

| | TNFα (Gene expression by relative quantity) | |
|---|---|---|
| Control tissue | 1.00 | |
| Injured tissue | 2.45 | +145% |
| Injured tissue + balm | 1.76 | −28% |

Tumor Necrosis Factor-alpha is an important inflammation mediator; the inflammatory signal contributes to the amplification of the pain experienced. The reconstructed skin lesion induced a strong increase (+145%) of TNFα gene expression, representative of induction of an inflammatory signal.

The topical application of the breastfeeding balm modulated the overexpression of TNFα by the lesion (−28%).

The breastfeeding balm modulates inflammation and therefore contributes to minimizing pain.

c. Evaluation of Barrier Repair: Expression of Filaggrin

Figure 5:
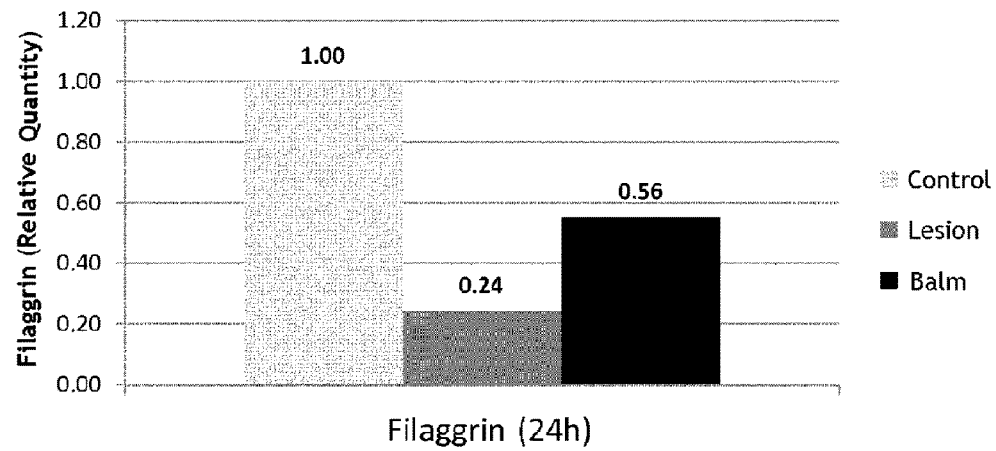

The filaggrin production measurement results are indicated in Table 3 and illustrated by FIG. 5.

TABLE 1

|  | Filaggrin (Gene expression by relative quantity) | |
| --- | --- | --- |
| Control tissue | 1.00 | |
| Injured tissue | 0.24 | −76% |
| Injured tissue + balm | 0.56 | +133% |

Filaggrin plays an essential double role in the barrier function: one the one hand, it aggregates to keratin fibers of the cytoskeleton, thus reducing corneocytes into flattened disks; this intracellular network provides strength and protection to the stratum corneum. On the other hand, filaggrin is the precursor for NMF (Natural Moisturizing Factor). NMF is highly hygroscopic and is essential to retaining water in corneocytes, it plays a major role in maintaining skin pH, thus regulating key biochemical events such as protease activity, barrier permeability and antimicrobial defences, functions that are fundamentally linked and co-regulated. The reconstructed skin lesion led to a substantial reduction (−76%) of filaggrin gene expression, showing significant impairment of the barrier function.

The application of the breastfeeding balm modulated filaggrin repression (+133%). The breastfeeding balm tends to counteract the harmful effect of the lesion on the barrier and thus contributes to accelerating barrier repair.

d. Evaluation on Healing Initiation: Expression of Integrin-$\beta 1$

Figure 6:
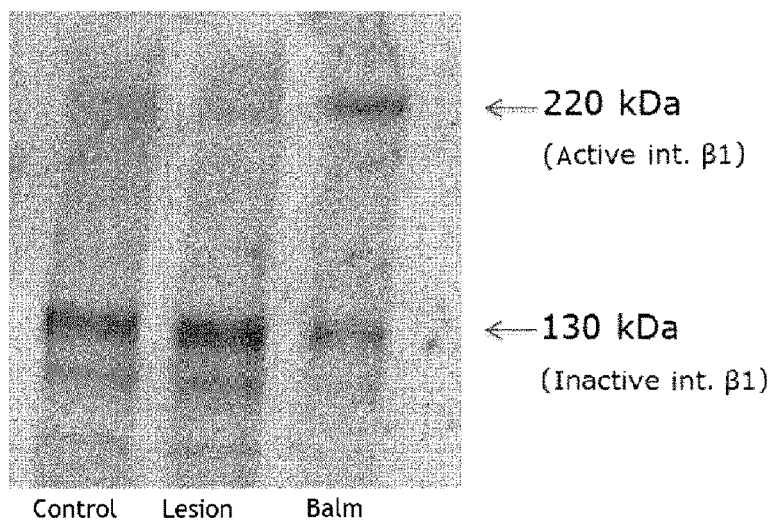

The integrin-$\beta 1$ production measurement results are illustrated by FIG. 6.

The integrins, a group of membrane proteins, are important factors in healing regulation. On the one hand, integrins help the migration of keratinocytes, an early step in the healing process; and on the other hand, they are bound to macromolecules of the dermal matrix, thus ensuring contact of the epidermis with the newly synthesized dermal extracellular matrix to permit cohesion and communication between the two compartments (dermis and epidermis).

The integrin $\beta 1$ subunit is a 130 kDa transmembrane protein that forms noncovalent complexes with different $\alpha$ subunits to form functional and active receptors.

These receptors coordinate the activation of intracellular signalling pathways particular involved in healing.

Western analysis of integrin $\beta 1$ production (FIG. 6) shows that:

in control and injured tissues, a single band of 130 kDa is observed; this band corresponds to the integrin $\beta 1$ subunit alone;

in the presence of the breastfeeding balm, the $\beta 1$ subunit alone (130 kDa band) decreases and aggregates of higher molecular weight (220 kDa) are formed; these aggregates correspond to the formation of complexes (subunit $\beta 1$ lined to an $\alpha$ subunit) or functional heterodimer receptors representative of the activation of integrin $\beta 1$.

The breastfeeding balm makes integrin $\beta 1$ functional and therefore permits initiating the healing process.

3. Conclusion

A nipple model obtained by skin reconstruction from a batch of keratinocytes overexpressing filaggrin was used in order to evaluate the reparative and antiinflammatory efficacy of a breastfeeding balm after injury of the nipple mimicking a crack.

In the injured nipple model, the breastfeeding balm has a protective effect (protection of the integrity of cell membranes/LDH), reparative effect (induction of healing/integrin $\beta 1$; restoration of the barrier/filaggrin and soothing effect (antiinflammatory/TNF$\alpha$)

These results confirm the usefulness of the model implemented as a model mimicking nipple skin and allowing the evaluation of the reparative and soothing efficacy of a formulation dedicated to nipple care, in particular in the case of appearance of cracks or fissures.

D. Study 2: Use of a Reconstructed Nipple Epidermis Model to Comparatively Evaluate the Reparative and Antiinflammatory Efficacy of Cosmetic Breastfeeding Products in Comparison to Breast Milk 1. Materials and Methods To mimic the nipple, a reconstructed epidermis, obtained from a batch of keratinocytes overexpressing filaggrin (as described previously), was used.

Two cosmetic products designed to care for cracks related to breastfeeding were studied: a breastfeeding balm (corresponding to the "breastfeeding balm 3" formulation) and an ointment based on lanolin (product 2). At the same time, breast milk, described for its reparative properties, was also evaluated.

A lesion (mechanical wound) was created on the surface of the nipple epidermis in order to mimic a nipple crack or fissure.

The test products were applied topically immediately after creating the lesion.

The reconstructed skin was then incubated for 4 hours and 24 hours and then the following parameters were analyzed:

Release of LDH;

Gene expression (real-time qPCR) of TGF $\beta 1$ and TNF$\alpha$;

Immunofluorescence labeling of integrin $\beta 1$ (only product 1).

a. Quantification of Released LDH:

The LDH released into the reconstructed epidermis culture medium was quantified by means of a colorimetric test based on the detection of formazan salts whose formation is related to the enzymatic activity of the enzyme. The quantity of LDH was determined using a standard curve and expressed in mU/ml.

b. Real-Time qPCR:

The reconstructed epidermises were lysed and the total RNAs extracted and then reverse transcribed into cDNA. The expression of the genes of interest (TNF$\alpha$, TGF $\beta 1$) was analyzed by real-time qPCR and compared to the expression of housekeeping gene GAPDH.

c. Immunofluorescence Labeling of Integrin $\beta 1$ (Evaluated Only for Product 1).

The reconstructed epidermises were fixed, coated in paraffin and sliced. The sections were incubated in the presence of a primary antibody directed against the extracellular domain of integrin $\beta 1$ (Santa Cruz), and the in the presence of a secondary antibody conjugated to fluorochrome Alexa Fluor 555 (Invitrogen). The nuclei were counterstained with DAPI.

The labeling was imaged by confocal microscope (Leica).

2. Results a. Evaluation of the Cell Membrane Integrity: LDH Assay

Figure 7:
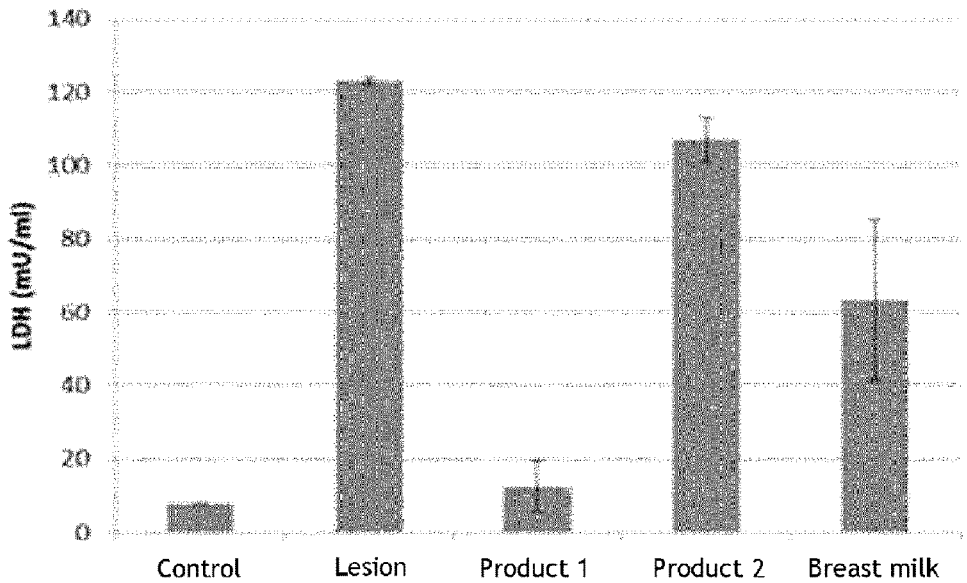

The results are presented in Table 4 and illustrated in FIG. 7.

TABLE 1

| | LDH (mU/ml) | |
| --- | --- | --- |
| Control tissue | 7.8 ± 0 | |
| Injured tissue | 123.11 ± 0.86 | |
| Injured tissue + product 1 | 12.45 ± 6.98 | −90% |
| Injured tissue + product 2 | 106.85 ± 6.06 | −13% |
| Injured tissue + breast milk | 63.15 ± 21.94 | −49% |

The reconstructed nipple epidermis lesion induced extensive release of LDH into the extracellular space, representative of the impaired integrity of the cell membranes.

The topical application of product 1 greatly reduced the release of LDH (90% inhibition). Product 2 tested slightly reduced LDH release (−13%) and breast milk led to an intermediate reduction of LDH release (−49%).

Product 1 and breast milk, to a lesser extent, protect tissue integrity and accelerate their recovery after injury.

b. Evaluation of the Inflammatory Response: Expression of TNFα

Figure 8:
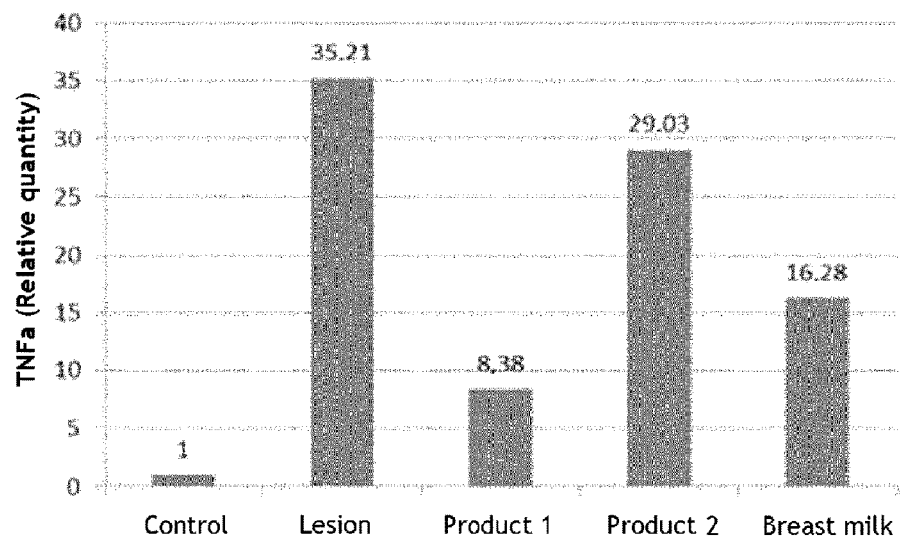

The results are presented in Table 5 and illustrated in FIG. 8.

TABLE 5

| | TNFα (Gene expression by relative quantity) | |
| --- | --- | --- |
| Control tissue | 1.00 | |
| Injured tissue | 35.21 | |
| Injured tissue + product 1 | 8.38 | −76% |
| Injured tissue + product 2 | 29.03 | −17% |
| Injured tissue + breast milk | 16.28 | −54% |

The reconstructed epidermis lesion induced a strong increase in TNFα gene expression, representative of induction of an inflammatory signal.

Product 1 very clearly inhibited TNFα expression induced by the lesion (−76%); product 2 induced a slight reduction (−17%) and breast milk induced an intermediate reduction (−54%).

Product 1 and, to a lesser extent, breast milk, modulate inflammation and contribute to pain relief.

c. Evaluation on Healing Initiation: Expression of TGF β1

Figure 9:
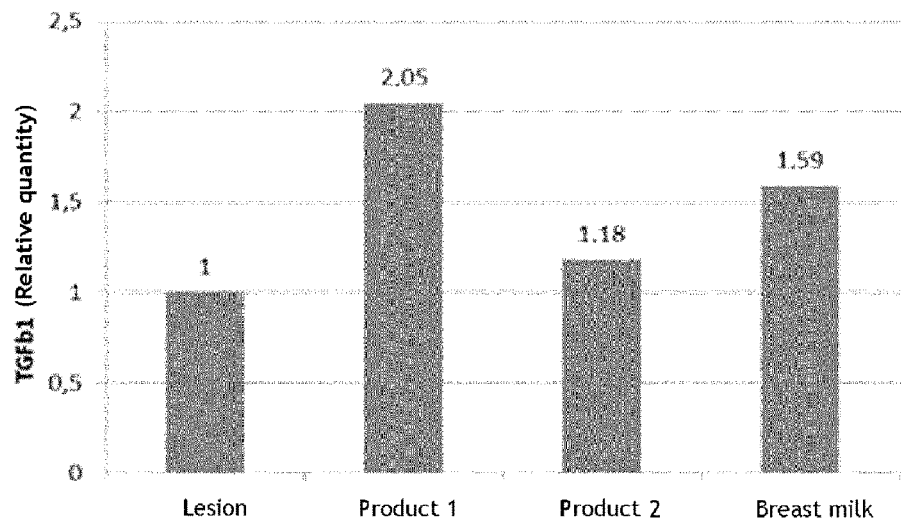

The results are presented in Table 6 and illustrated in FIG. 9.

TABLE 6

| | TGF β1 (Gene expression by relative quantity) | |
| --- | --- | --- |
| Injured tissue | 1.00 | |
| Injured tissue + product 1 | 2.05 | +105% |
| Injured tissue + product 2 | 1.18 | +18% |
| Injured tissue + breast milk | 1.59 | +59% |

TGF β1 is a growth factor that controls numerous cell functions; it is notably involved in the regulation of healing and in stimulating the re-epithelization phase early in the epidermal healing phase.

Product 1 induced a substantial increase (+105%) in TGF β1 expression in injured tissues, product 2 led to a slight increase (+18%) and breast milk led to an intermediate increase (+59%).

Product 1 and, to a lesser extent, breast milk, contribute to initiating the healing process for a reparative effect.

d. Evaluation on Healing Initiation: Expression of Integrin β1

Figure 10:
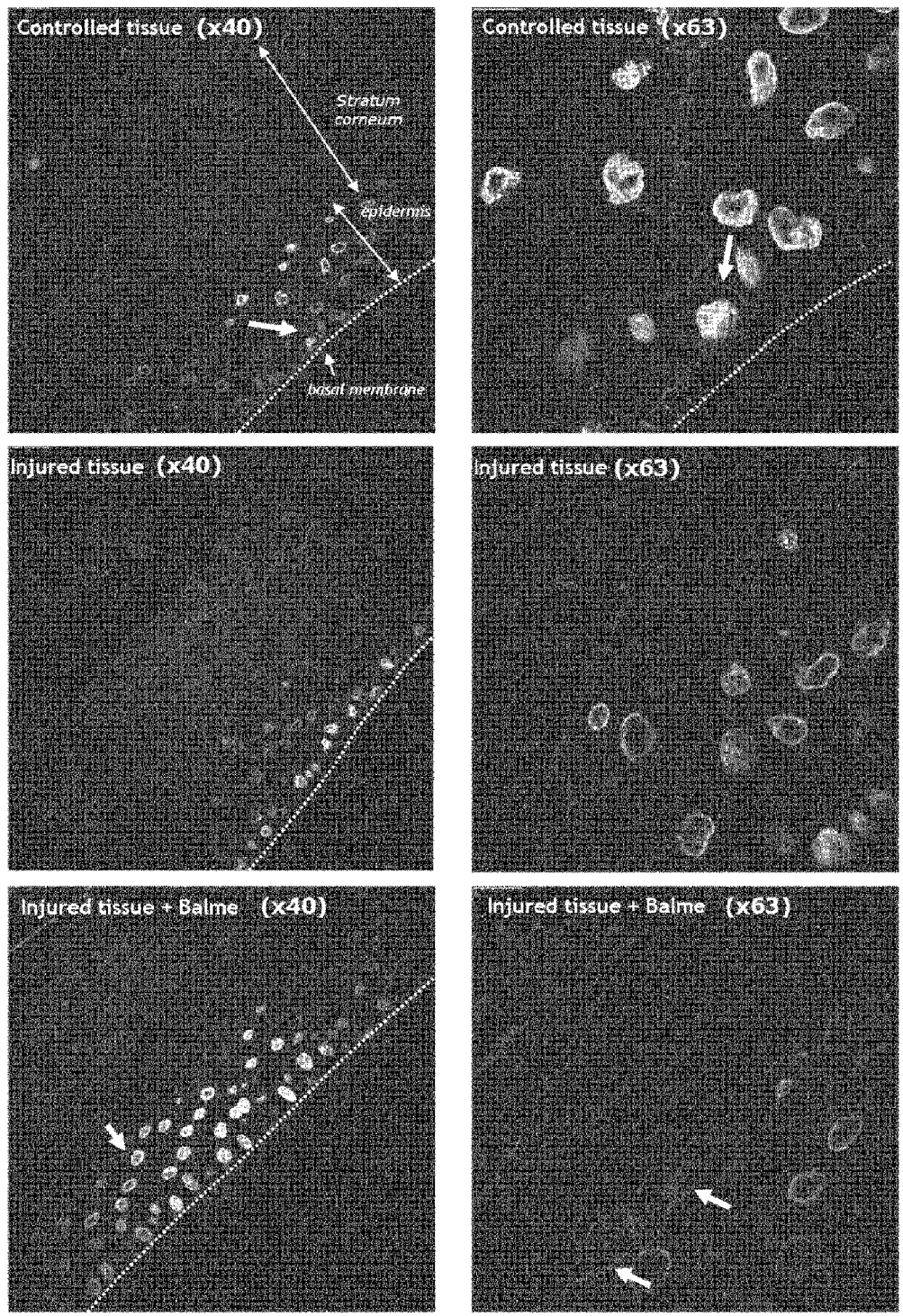

The results are illustrated in FIG. 10.

In the control tissues, the results show an intense labeling of integrin β1 associated with the plasma membrane of keratinocytes (yellow arrows). This membrane location for integrin β1 shows the availability/functionality of the receiver.

The tissue lesion leads to a strong decrease of integrin β1 labeling; this latter has practically disappeared, which shows an alteration of the receptor.

In the presence of a breastfeeding balm (product 1), membrane labeling of integrin β1 is recovered (yellow arrows) which bears witness to the restoration of receptor functionality.

The breastfeeding balm (product 1) restores the production of integrin β1, therefore restoring intercellular contacts to initiate the repair process.

3. Conclusion

A nipple model obtained by reconstruction of an epidermis from a batch of keratinocytes overexpressing filaggrin was used in order to comparatively evaluate the reparative and antiinflammatory efficacy of cosmetic products intended for nipple care in comparison with breast milk. The reconstructed nipple epidermis was injured on the surface in order to mimic a lesion.

On this injured nipple epidermis model, efficacy differences were found between the two products tested and breast milk (known for its reparative properties) in terms of protective action (protection of cell membrane integrity/LDH), repair (initiation of wound healing/TGF β1, integrin β1) and healing (anti-inflammatory/TNF).

These results confirm the usefulness of the model implemented as a model mimicking nipple epidermis, allowing the evaluation of different formulas and the identification of effective formulas for care of nipple cracks/fissures.

E. Study 3: Use of a Reconstructed Nipple Epidermis Model to Show the Protective and Reparative Effect of a Breastfeeding Balm.

The preceding steps showed the usefulness of the nipple model implemented for evaluation of the activity or identification of a formulation to treat nipple skin lesions relying on measurement of markers of a reparative, protective or antiinflammatory effect.

In order to validate the conclusions obtained by the analysis of the marker production level, we sought to show the effect of a lesion in the nipple epidermal model and the reparative effect of a product by using the electron microscope technique.

1. Materials and Methods

A reconstructed epidermis, obtained from a batch of keratinocytes overexpressing filaggrin (as described previously), was used as a nipple model.

A lesion (mechanical wound) was created on the surface of the nipple epidermis in order to mimic a nipple crack or fissure.

A breastfeeding balm corresponding to the "breastfeeding balm 3" formulation was then applied topically.

After incubation for 4 hours, the epidermises were fixed, dehydrated and covered with a layer of gold before being observed in the scanning electron microscope (Zeiss).

2. Results

The results are illustrated in FIG. 11.

Epidermal keratinocytes form a corneal envelope during the final steps of their differentiation. This corneal envelope ensures the cohesion and solidarity of the stratum corneum and plays a vital role in the epidermis barrier function.

SEM observation of the reconstructed tissue surface shows, in the control tissues, an intact cutaneous surface, homogenous and smooth (corresponding to the corneal envelope) where cell outlines are distinguished (corneocytes; blue arrow).

The lesion caused a deep wound with destruction of the corneal envelope.

The application of the breastfeeding balm after the lesion visibly accelerates the repair of this wound: the surface is more regular and smoother, showing restoration of the corneal envelope.

3. Conclusion

These SEM observations directly confirm the reparative and protective effect of the breastfeeding balm shown by the production of different markers during the preceding steps.

Thus these results confirm:

the usefulness of the model implemented as a model mimicking cracked nipple skin or epidermis permitting evaluating or identifying the reparative or protective effect of a formulation, the choice of markers (in the preceding steps) and their validity as markers representative of a reparative and protective effect.

The invention claimed is:

1. An in vitro reconstructed nipple skin model comprising keratinocytes of human origin overexpressing filaggrin and a lesion, wherein said keratinocytes constitutively express filaggrin at a level greater than the filaggrin expression level of healthy human primary keratinocytes.

2. The model of claim 1, wherein said model comprises a support matrix.

3. The model of claim 2, wherein said support matrix is inoculated with fibroblasts.

4. A method, comprising:
   a) contacting an active ingredient or a formulation with the nipple skin model of claim 1;
   b) measuring the production level of a biological marker in the nipple skin model of step a), wherein said biological marker is selected from the group consisting of:
      epidermal integrity markers;
      epidermal barrier markers;
      epidermal inflammation markers; and
      healing markers
   c) measuring a reference production level of said biological marker in a skin model according to claim 1 that has not been contacted with said active ingredient or said formulation, or that has been contacted with a reference active ingredient or formulation,
   d) preparing a dermatological formulation comprising the candidate active ingredient or candidate formulation if:
      (i) the production level of said biological marker measured in step b) is less than or equal to the reference production level of said biological marker measured in step c) when said biological marker is an epidermal integrity marker or an epidermal inflammation marker, or
      (ii) the production level of said biological marker measured in step b) is greater than or equal to the reference production level of said biological marker measured in step c) when said biological marker is an epidermal barrier marker or a healing marker.

5. The method of claim 4, further comprising administering an effective amount of the dermatological formulation to a human patient presenting a nipple skin lesion or nipple skin inflammation.

6. The method of claim 4, wherein step b) comprises measuring the production level of two biological markers.

7. The model of claim 1, wherein the lesion is a linear ulceration.

8. The method of claim 4, wherein said epidermal integrity marker is lactate dehydrogenase (LDH).

9. The method of claim 4, wherein said epidermal barrier marker is filaggrin.

10. The method of claim 4, wherein said epidermal inflammation marker is selected from cytokines.

11. The method of claim 4, wherein said epidermal inflammation marker is TNFα.

12. The method of claim 4, wherein said healing marker is selected from integrins.

13. The method of claim 4, wherein said healing marker is integrin β1 or TGF β1.

14. The method of claim 5, wherein said nipple skin lesion is a linear ulceration.

15. The method of claim 4, wherein the production level of said biological marker is measured using an enzymatic test when said biological marker is the product of a gene with an enzymatic activity.

16. The method of claim 15, wherein said marker is lactate dehydrogenase (LDH).

17. The method of claim 4, wherein the production level of said biological marker is measured using analysis of the transcriptome, RT-PCR, quantitative RT-PCR, or nucleic acid chips when said biological marker is a gene.

18. The method of claim 17, wherein said biological marker is lactate dehydrogenase (LDH), TNFα, TGF β1, or filaggrin.

19. The method of claim 4, wherein the production level of said biological marker is measured using immunoassays when said biological marker is a polypeptide or the product of a gene.

20. The method of claim 19, wherein said biological marker is integrin β1.

21. The model of claim 1, wherein said lesion is a lesion mimicking a crack.

* * * * *